(12) United States Patent
Harris et al.

(10) Patent No.: US 11,061,094 B2
(45) Date of Patent: Jul. 13, 2021

(54) SIMULTANEOUS PH AND OXYGEN WEIGHTED MRI CONTRAST USING MULTI-ECHO CHEMICAL EXCHANGE SATURATION TRANSFER IMAGING (ME-CEST)

(71) Applicant: The Regents of the University of California, Oakland, CA (US)

(72) Inventors: Robert Harris, Los Angeles, CA (US); Kevin Leu, San Diego, CA (US); Benjamin Ellingson, Redondo Beach, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/614,893

(22) PCT Filed: May 22, 2018

(86) PCT No.: PCT/US2018/033973
§ 371 (c)(1),
(2) Date: Nov. 19, 2019

(87) PCT Pub. No.: WO2018/217817
PCT Pub. Date: Nov. 29, 2018

(65) Prior Publication Data
US 2020/0158803 A1    May 21, 2020

Related U.S. Application Data

(60) Provisional application No. 62/509,355, filed on May 22, 2017.

(51) Int. Cl.
*G01R 33/50* (2006.01)
*A61K 49/10* (2006.01)
(Continued)

(52) U.S. Cl.
CPC ............ *G01R 33/50* (2013.01); *A61K 49/105* (2013.01); *G01R 33/4804* (2013.01);
(Continued)

(58) Field of Classification Search
USPC .......................................... 324/309
See application file for complete search history.

(56) References Cited

U.S. PATENT DOCUMENTS 8,395,385 B2 *   3/2013   Lee .................... G01R 33/4835
                                                         324/307
2014/0375314 A1   12/2014  Buckner
(Continued)

FOREIGN PATENT DOCUMENTS

WO   2016196392 A1   12/2016
WO   2017040368 A1   3/2017

OTHER PUBLICATIONS

Stadlbauer A, et al. MR Imaging-derived oxygen metabolism and neovascularization characterization for grading and IDH gene mutation detection of gliomas. Radiology. 2016:161422.
(Continued)

*Primary Examiner* — Rodney E Fuller
(74) *Attorney, Agent, or Firm* — Quarles & Brady LLP

(57) ABSTRACT

The present disclosure provides a method that includes applying at least one radiofrequency saturation pulse at a frequency or a range of frequencies to substantially saturate magnetization corresponding to an exchangeable proton in the ROI to generate magnetic resonance (MR) data. The MR data is then acquired using an echo-planar imaging readout, which is configured to sample a series of gradient echo pulse trains at a series of gradient echo times and a series of spin echo pulse trains at a series of spin echo times. One or more relaxometry measurement is then computed using the MR data sampled at the gradient echo times and the spin echo
(Continued)

times. An oxygen-weighted image is then generated using the one or more relaxometry measurement, and a pH-weighted image is generated using MR data sampled at one or more of the spin echo times or gradient echo times.

21 Claims, 11 Drawing Sheets

(51) Int. Cl.
G01R 33/48 (2006.01)
G01R 33/483 (2006.01)
G01R 33/56 (2006.01)
G01R 33/561 (2006.01)

(52) U.S. Cl.
CPC ..... *G01R 33/4828* (2013.01); *G01R 33/4838* (2013.01); *G01R 33/5602* (2013.01); *G01R 33/5608* (2013.01); *G01R 33/5616* (2013.01)

(56) References Cited

U.S. PATENT DOCUMENTS

| | | | |
|---|---|---|---|
| 2015/0338483 | A1 | 11/2015 | Sun |
| 2016/0038727 | A1 | 2/2016 | Emami et al. |
| 2016/0139228 | A1 | 5/2016 | McMahon |
| 2017/0089995 | A1* | 3/2017 | Basser ............... G01R 33/5608 |
| 2017/0176563 | A1* | 6/2017 | Yablonskiy ........... G01R 33/50 |
| 2018/0249925 | A1 | 9/2018 | Ellingson |
| 2018/0252789 | A1 | 9/2018 | Ellingson |
| 2018/0275235 | A1* | 9/2018 | Reeder ................ G01R 33/543 |

OTHER PUBLICATIONS

Sun PZ, et al. Early experience of translating pH-weighted MRI to image human subjects at 3 Tesla. Stroke. 2010;41: S147-S151.
Sun PZ, et al. Sensitivity-enhanced chemical exchange saturation transfer (CEST) MRI with least squares optimization of Carr Purcell Meiboom Gill multi-echo echo planar imaging. Contrast Media Mol Imaging. 2014;9:177-181.
Togao O, et al. Amide proton transfer imaging of adult diffuse gliomas: correlation with histopathological grades. Neuro Oncol. 2014;16:441-448.
Togao O, et al. Scan-rescan reproducibility of parallel transmission based amide proton transfer imaging of brain tumors. J Magn Reson Imaging. 2015;42: 1346-1353.
Toth V, et al. MR-based hypoxia measures in human glioma. J Neurooncol. 2013;115:197-207.
Turner GA. Increased release of tumour cells by collagenase at acid pH: a possible mechanism for metastasis. Experientia. 1979;35:1657-1658.
Ulrich X, et al. Separation of cellular and BOLD contributions to T2* signal relaxation. Magn Reson Med. 2016; 75:606-615.
Vaishnavi, S.N. et al, Regional aerobic glycolysis in the human brain, Proc Natl Acad Sci U S A, 107 (2010) 17757-17762.
Valk, P.E. et al, Hypoxia in human gliomas: demonstration by PET with fluorine-18-fluoromisonidazole, J Nucl Med, 33 (1992) 2133-2137.
Vlassenko, A.G. et al, Aerobic Glycolysis as a Marker of Tumor Aggressiveness: Preliminary Data in High Grade Human Brain Tumors, Dis Markers, 2015 (2015) 874904.
Woessner DE, et al. Numerical solution of the Bloch equations provides insights into the optimum design of PARACEST agents for MRI. Magn Reson Med. 2005;53:790-799.
Wolf A, et al. Hexokinase 2 is a key mediator of aerobic glycolysis and promotes tumor growth in human glioblastoma multiforme. J Exp Med. 2011;208:313-326.
Wu, W. et al, Metabolic changes in cancer: beyond the Warburg effect, Acta Biochim Biophys Sin (Shanghai), 45 (2013)18-26.

Xu X, et al. Dynamic glucose-enhanced (DGE) MRI: translation to human scanning and first results in glioma patients. Tomography. 2015;1:105-114.
Zaiss M, et al. Quantitative separation of CEST effect from magnetization transfer and spillover effects by Lorentzian-ine-fit analysis of z-spectra. J Magn Reson. 2011; 211:149-155.
Zaiss M, et al. Relaxation-compensated CEST-MRI of the human brain at 7 T: unbiased insight into NOE and amide signal changes in human glioblastoma. NeuroImage. 2015;112:180-188.
Zhang J, et al. Blood-oxygenation-level-dependent-(BOLD-) based R2' MRI study in monkey model of reversible middle cerebral artery occlusion. J Biomed Biotechnol. 2011;2011:318346.
Zhu XH, et al. In vivo (17)O NMR approaches for brain study at high field. NMR Biomed. 2005;18:83-103.
Zu ZL, et al. A new method for detecting exchanging amide protons using chemical exchange rotation transfer. Magn Reson Med. 2013;69:637-647.
Borodovsky A, et al. Altered cancer cell metabolism in gliomas with mutant IDH1 or IDH2. Curr Opin Oncol. 2012;24:83-89.
Brat DJ, et al. Pseudopalisades in glioblastoma are hypoxic, express extracellular matrix proteases, and are formed by an actively migrating cell population. Cancer Res. 2004;64:920-927.
Bryant RG. The dynamics of water-protein interactions. Annu Rev Biophys Biomol Struct. 1996;25:29-53.
Da Ponte KF, et al. In vivo relationship between hypoxia and angiogenesis in human glioblastoma: a multimodal imaging study. J Nucl Med. 2017;58:1574-1579.
Deberardinis, R.J. Is cancer a disease of abnormal cellular metabolism? New angles on an old idea, Genet Med, 10 (2008) 767-777.
Domsch S, et al. Non-invasive multi-parametric qBOLD approach for robust mapping of the oxygen extraction fraction. Z Med Phys. 2014;24:231-242.
Flynn Jr, et al. Hypoxia-regulated protein expression, patient characteristics, and preoperative imaging as predictors of survival in adults with glioblastoma multiforme. Cancer. 2008;113:1032-1042.
Fujita N, et al. Quantitative mapping of cerebral deoxyhemoglobin content using MR imaging. NeuroImage. 2003;20:2071-2083.
Gatenby RA, et al. An evolutionary model of carcinogenesis. Cancer Res. 2003;63:6212-6220.
Gatenby RA, et al. Why do cancers have high aerobic glycolysis? Nat Rev Cancer. 2004;4:891-899.
Geisler BS, et al. Blood oxygen level-dependent MRI allows metabolic description of tissue at risk in acute stroke patients. Stroke. 2006;37:1778-1784.
Griffiths L, et al. The influence of oxygen tension and pH on the expression of platelet-derived endothelial cell growth factor/thymidine phosphorylase in human breast tumor cells grown in vitro and in vivo. Cancer Res. 1997;57:570-572.
Harris RJ, et al. pH-weighted molecular imaging of gliomas using amine chemical exchange saturation transfer MRI. Neuro Oncol. 2015;17:1514-1524.
Harris RJ, et al. Simulation, phantom validation, and clinical evaluation of fast pH-weighted molecular imaging using amine chemical exchange saturation transfer echo planar imaging (CEST-EPI) in glioma at 3 T. NMR Biomed. 2016;29:1563-1576.
He X, et al. Validation of oxygen extraction fraction measurement by qBOLD technique. Magn Reson Med. 2008;60:882-888.
Heo HY, et al. Accelerating chemical exchange saturation transfer (CEST) MRI by combining compressed sensing and sensitivity encoding techniques. Magn Reson Med. 2017;77:779-786.
Hirsch NM, et al. Technical considerations on the validity of blood oxygenation level-dependent-based MR assessment of vascular deoxygenation. NMR Biomed. 2014;27:853-862.
Hua J, et al. Quantitative description of the asymmetry in magnetization transfer effects around the water resonance in the human brain. Magn Reson Med. 2007;58:786-793.
International Searching Authority, International Search Report and Written Opinion for application PCT/US2018/033973, dated Aug. 9, 2018.
Jensen-Kondering U, et al. Brain hypoxia mapping in acute stroke: back-to-back T2' MR versus (18)F-fluoromisonidazole PET in rodents. Int J Stroke. 2017;12: 752-760.

(56) References Cited

OTHER PUBLICATIONS

Jensen-Kondering U, et al. Oxygen imaging by MRI: Can blood oxygen level-dependent imaging depict the Ischemic penumbra? Stroke. 2012;43:2264-2269.
Jin T, et al. Mapping brain glucose uptake with chemical exchange-sensitive spin-lock magnetic resonance imaging. J Cereb Blood Flow Metab. 2014;34:14021410.
Jin T, et al. MR imaging of the amide-proton transfer effect and the pH-insensitive nuclear Overhauser effect at 9.4 T. Magn Reson Med. 2013;69:760-770.
Jones CK, et al. Nuclear Overhauser enhancement (NOE) imaging in the human brain at 7T. NeuroImage. 2013;77:114-124.
Kim M, et al. Water saturation shift referencing (WASSR) for chemical exchange saturation transfer (CEST) experiments. Magn Reson Med. 2009;61: 1441-1450.
Kovacevic Z, et al. The role of glutamine in the oxidative metabolism of malignant cells. Cancer Res. 1972;32:326-333.
Lardner A. The effects of extracellular pH on immune function. J Leukoc Biol. 2001;69:522-530.
Lee DH, et al. Quantitative assessment of the effects of water proton concentration and water T-1 changes on amide proton transfer (APT) and nuclear overhauser enhancement (NOE) MRI: the origin of the APT imaging signal in brain tumor. Magn Reson Med. 2017;77:855-863.
Liepinsh E, et al. Proton exchange rates from amino acid side chains—implications for image contrast. Magn Reson Med. 1996;35:30-42.
Martinez-Zaguilan R, et al. Acidic pH enhances the invasive behavior of human melanoma cells. Clin Exp Metastasis. 1996;14:176-186.
Maurer GD, et al. Differential utilization of ketone bodies by neurons and glioma cell lines: a rationale for ketogenic diet as experimental glioma therapy. BMC Cancer. 2011;11:315.
Medina MA, et al. Relevance of glutamine metabolism to tumor cell growth. Mol Cell Biochem. 1992;113:1-15.
Mellon EA, et al. Estimation of the regional cerebral metabolic rate of oxygen consumption with proton detected O-17 MRI during precision O-17(2) inhalation in swine. J Neurosci Methods. 2009;179:29-39.
Mendichovszky, I. et al, Imaging hypoxia in gliomas, Br J Radiol, 84 Spec No. 2 (2011) S145-158.
Morita T, et al. Clastogenicity of low pH to various cultured mammalian cells. Mutat Res. 1992; 268:297-305.
Nasrallah FA, et al. Imaging brain deoxyglucose uptake and metabolism by glucoCEST MRI. J Cereb Blood Flow Metab. 2013;33:1270-1278.
Nie S, et al. miR-495 mediates metabolic shift in glioma cells via targeting Glut1. J Craniofac Surg. 2015;26:e155-e158.

Noordin S, et al. Factors affecting paramagnetic contrast enhancement in synovial fluid: effects of electrolytes, protein concentrations, and temperature on water proton relaxivities from Mn ions and Gd chelated contrast agents. Osteoarthritis Cartilage 2010;18:964-970.
Ogawa S, et al. Brain magnetic resonance imaging with contrast dependent on blood oxygenation. Proc Natl Acad Sci U S A. 1990;87:9868-9872.
Paech D, et al. T1rho-weighted dynamic glucose-enhanced MR imaging in the human brain. Radiology. 2017;285:914-922.
Perry TL, et al. Free amino acids and related compounds in biopsies of human brain. J Neurochem. 1971;18:521-528.
Pugh CW, et al. Regulation of angiogenesis by hypoxia: role of the HIF system. Nat Met 2003;9:677-684.
Schmiedeskamp H, et al. Combined spin-and gradient-echo perfusion-weighted imaging. Magn Reson Med. 2012;68:30-40.
Schmiedeskamp H, et al. Compensation of slice profile mismatch in combined spinand gradient-echo echo-planar Imaging pulse sequences. Magn Reson Met 2012;67:378388.
Schuenke P, et al. Adiabatically prepared spin-lock approach for T1rho-based dynamic glucose enhanced MRI at ultrahigh fields. Magn Reson Med. 2017;78: 215-225.
Sherry, A.D., et al. "Chemical exchange saturation transfer contrast agents for magnetic resonance imaging." Annu. Rev. Biomed. Eng. 10 (2008): 391-411.
Shi Q, et al. Regulation of vascular endothelial growth factor expression by acidosis in human cancer cells. Oncogene. 2001;20:3751-3756.
Song X, et al. Multi-echo length and offset VARied saturation (MeLOVARS) method for improved CEST imaging. Magn Reson Med. 2015;73:488-496.
Sottoriva A, et al. Intratumor heterogeneity in human glioblastoma reflects cancer evolutionary dynamics. Proc Natl Acad Sci U S A. 2013;110:4009-4014.
Souba WW. Glutamine and cancer. Ann Surg. 1993;218:715-728.
European Patent Office. Extended European Search Report for application 18805390. dated Jan. 25, 2021. 10 pages.
Harris RJ, et al. A "Glycolytic Index" for quantifying abnormal metabolism in human gliomas using multi-echo amine chemical exchange saturation transfer spin-and-gradient echo echoplanar imaging (ME-aCEST-SAGE-EPI) at 3T. Proceedings of the ISMRM 25th Annual Meeting and Exhibition, Honolulu, HI, USA, Apr. 22,-Apr. 27, 2017, No. 1104, Apr. 7, 2017.
Harris RJ, et al. "Simultaneous p H-sensitive and oxygen-sensitive MRI of human gliomas at 3 T using multi-echo amine proton chemical exchange saturation transfer spin-and-gradient echo echoplanar imaging (CEST-SAGE-EPI)". Magnetic resonance in medicine 80.5 (2018): 1962-1978.

\* cited by examiner

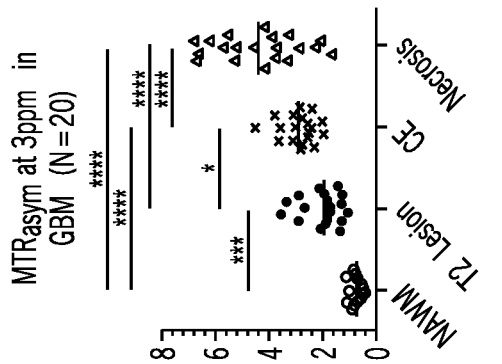
FIG. 15
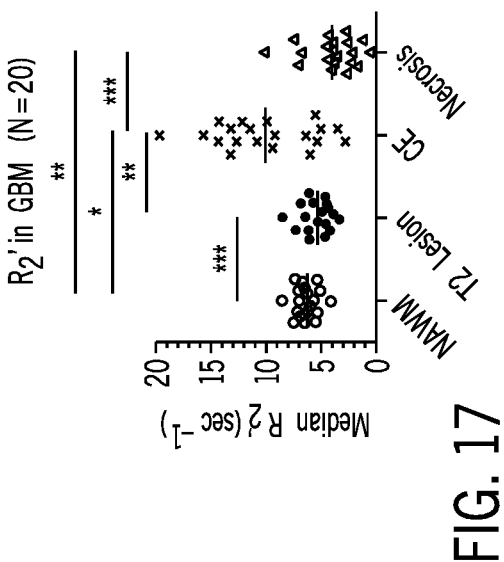
FIG. 16
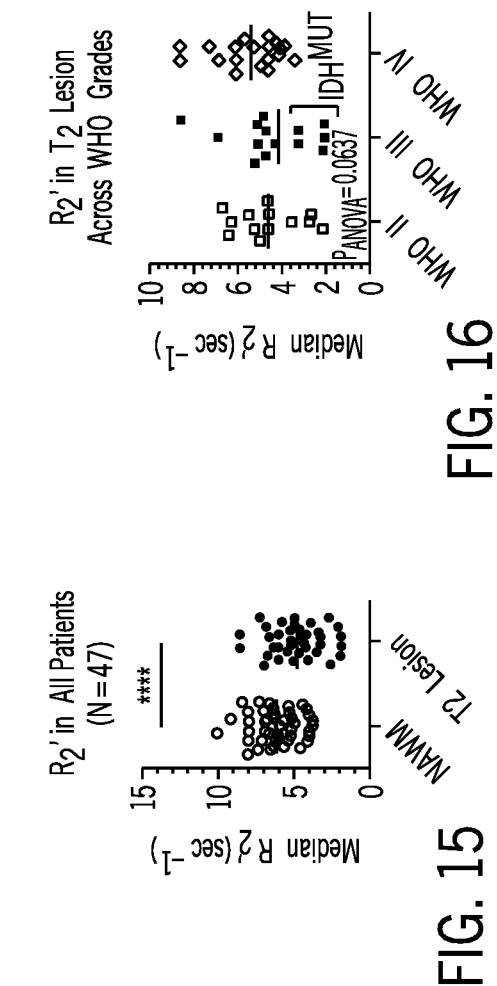
FIG. 17
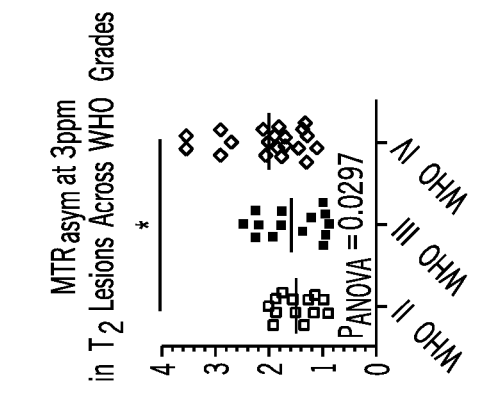
FIG. 18
FIG. 19
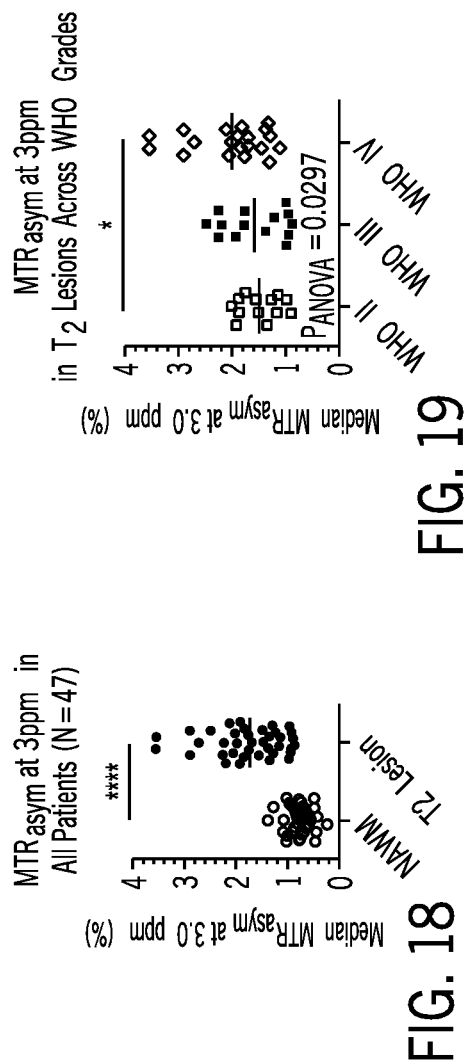
FIG. 20

SIMULTANEOUS PH AND OXYGEN WEIGHTED MRI CONTRAST USING MULTI-ECHO CHEMICAL EXCHANGE SATURATION TRANSFER IMAGING (ME-CEST)

CROSS-REFERENCE TO RELATED APPLICATIONS

The present application represents the national stage entry of International Application PCT/US2018/033973, filed May 22, 2018, which claims priority to U.S. Provisional Application Ser. No. 62/509,355, filed on May 22, 2017, the entire contents of which are herein incorporated by reference.

BACKGROUND

Abnormal metabolism is a hallmark of cancer. Notably, glycolysis is often enhanced in cancers, even in the presence of abundant oxygen. This process is known as the Warburg effect, and is illustrated schematically in FIG. 1. This form of aerobic glycolysis results in a dramatic decrease in extracellular pH due to increased concentration of lactic acid. Increasing extracellular acidity comes with dramatic consequences, as increased acidity can be directly linked to the degree of tumor aggressiveness and increases tumor invasion. Interestingly, histological evidence suggests regions containing pseudopalisades, a pathological trademark of glioblastoma, are also hypoxic, express extracellular matrix proteases, and are the result of active tumor migration.

Increased acidity within the tumor also has been shown to lead to decreased immune function. The acidic microenvironment in tumors is also conducive to elevated vascular endothelial growth factor expression and expression of platelet-derived endothelial cell growth factor, which has been shown to result in increased angiogenesis. This in turn leads to a positive feedback process, leading to further tumor growth, decreasing oxygen tension, increased hypoxia, and increasing glycolysis, resulting in increased lactic acid, decreasing extracellular tissue pH, and more mutations and/or adaptations of the tumor genome. Thus, extensive in vitro, preclinical, and clinical evidence appears to support the hypothesis that tumor acidity and oxygen metabolism both play a critical role in gliomagenesis.

Currently, there is a need in furthering our understanding of the role of extracellular acidosis and oxygen metabolism in human gliomas and its clinical relevance due to the lack of a robust noninvasive tool for simultaneously estimating and localizing regions of low pH and oxygen consumption.

SUMMARY OF THE PRESENT DISCLOSURE

The presented disclosure relates to systems and methods for generating, sometimes simultaneously, a pH-weighted image and an oxygen-weighted image using a magnetic resonance imaging (MRI) system. In some forms, the present disclosure provides a method for generating fast, non-invasive, and high resolution pH-sensitive and oxygen-sensitive contrast maps by using a MRI pulse sequence herein referred to as chemical exchange saturation transfer (CEST) spin-and-gradient echo (SAGE) echo-planar imaging (EPI), or (CEST-SAGE-EPI). Advantageously, the CEST-SAGE-EPI technique may simultaneously produce pH-weighted and oxygen-weighted image contrasts for evaluation of tissue microenvironments.

In one configuration, the method includes applying at least one radiofrequency (RF) saturation pulse at a frequency or a range of frequencies to substantially saturate magnetization corresponding to an exchangeable proton in the region of interest to generate magnetic resonance data. The magnetic resonance data generated in response to the RF saturation pulse is then acquired by performing an echo-planar imaging (EPI) readout. The EPI readout may be configured to acquire the magnetic resonance data by sampling a series of gradient echo pulse trains at a series of gradient echo times and sampling a series of spin echo pulse trains at a series of spin echo times. For example, the EPI readout may be configured to acquire the magnetic resonance data in each of a series of repetition time periods a first gradient echo pulse train at a first echo time, a second gradient echo pulse train at a second echo time, a first spin echo pulse train at a third echo time, and a second spin echo train at a fourth echo time.

One or more relaxometry measurement is then computed using the magnetic resonance data. For example, data sampled from the first echo time, the second echo time, the third echo time, and the fourth echo time may be used to compute the one or more relaxometry measurement. A oxygen-weighted image may then be generated based on the one or more relaxometry measurement, and a pH-weighted image may be generated using sampled magnetic resonance data at one or more of the gradient echo times or spin echo times. For example, the pH-weighted image may be generated using one or more of the first echo time, the second echo time, the third echo time, and the fourth echo time. In some aspects, the pH-weighted image is indicative of a concentration of the exchangeable proton within the region of interest, and the oxygen-weighted image is indicative of a concentration of deoxyhemoglobin within the region of interest. In some forms the pH-weighted image and the oxygen-weighted image are generated simultaneously.

In one configuration, the magnetic resonance data may comprise chemical exchange saturation transfer (CEST) data, and the method may further comprise processing the CEST data to generate a magnetization transfer ratio ($MTR_{asym}$) corresponding to the exchangeable proton within the region of interest, and wherein the pH-weighted image includes a contrast map of the magnetization transfer ratio. The exchangeable proton of interest may comprise an amine moiety, where the method would then include applying the at least one RF saturation pulse at a range of frequencies corresponding to an amine exchangeable proton in the region of interest.

In one configuration, the one or more relaxometry measurement includes a reversible transverse relaxation rate ($R'_2$), where the reversible transverse relaxation rate is then used to generate the oxygen-weighted image. The oxygen-weighted image may include a contrast map of the reversible transverse relaxation rate, which may be indicative of the deoxyhemoglobin concentration within the region of interest.

In one configuration, the first spin echo in the EPI readout comprises an asymmetric spin echo pulse train.

In one configuration, the pH-weighted image is generated using magnetic resonance data acquired at the first echo time and the second echo time. In some forms, the data acquired at the first echo time and the second echo time may be averaged to generate the pH-weighted image.

In one configuration, the at least one radiofrequency saturation pulse includes off-resonance chemical exchange saturation transfer (CEST) RF pulses, wherein the off-resonance CEST RF pulses includes a train of three Guassian pulses. In some forms, the at least one radiofrequency (RF) saturation pulse includes a spectral-spatial water excitation pulse configured before the echo-planar imaging readout. In one form, a refocusing pulse is configured between the second gradient echo pulse train and the first spin echo pulse train. The refocusing pulse may comprise a 180 degree refocusing pulse.

In one configuration, the region of interest includes a suspected ischemic region on the subject, and wherein the method further comprises displaying the pH-weighted image and the oxygen-weighted image on a display. In some forms, and the pH-weighted image is generated to exhibit a positive contrast for ischemic regions, and the oxygen-weighted image is configured to display a negative contrast for ischemic regions.

In one configuration, the region of interest includes a suspected traumatic injury that includes micro- or macroscopic bleeding, and wherein the method further comprises displaying the pH-weighted image and the oxygen-weighted image on a display. In some forms, the pH-weighted image is generated to exhibit a negative contrast for regions that include micro- or macroscopic bleeding, and the oxygen-weighted image is configured to display a positive contrast for regions that include micro- or macroscopic bleeding.

In another configuration, a method is provided for producing a pH-sensitive and an oxygen-sensitive magnetic resonance (MR) image in a region of interest of a subject. The method includes applying at least one radiofrequency (RF) saturation pulse at a frequency or a range of frequencies to substantially saturate magnetization corresponding to an exchangeable proton in the region of interest to generate magnetic resonance data. The method further includes performing an echo-planar imaging (EPI) readout to acquire magnetic resonance data in response to applying the at least one RF saturation pulse by sampling a series of gradient echo pulse trains at a series of gradient echo times and sampling a series of spin echo pulse trains at a series of spin echo times. One or more relaxometry measurement is then computed using the magnetic resonance data sample at the gradient echo times and the spin echo times. The method further includes generating an oxygen-weighted image based on the one or more relaxometry measurement, and generating a pH-weighted image based on the magnetic resonance data sampled at one or more of the gradient echo times and spin echo times. In some forms, the pH-weighted image and the oxygen-weighted image are generated simultaneously.

In another configuration, the magnetic resonance data comprises chemical exchange saturation transfer (CEST) data, and the method further comprises processing the CEST data to generate a magnetization transfer ratio ($MTR_{asym}$) corresponding to the exchangeable proton within the region of interest. In some forms, the pH-weighted image includes a contrast map of the magnetization transfer ratio.

In another configuration, the one or more relaxometry measurement includes a reversible transverse relaxation rate ($R'_2$). In some forms, the oxygen-weighted image includes a contrast map of the reversible transverse relaxation rate.

In one configuration, a system is provided that includes a magnet system configured to generate a polarizing magnetic field about at least a portion of a subject. The system also includes a magnetic gradient system including a plurality of magnetic gradient coils configured to apply at least one magnetic gradient field to the polarizing magnetic field, and a radio frequency (RF) system configured to apply an RF field to the subject and to receive magnetic resonance signals from the subject using a coil array. The system may further include a computer system programmed to: apply at least one radiofrequency (RF) saturation pulse at a frequency or a range of frequencies to substantially saturate magnetization corresponding to an exchangeable proton in the region of interest to generate magnetic resonance data, and perform an echo-planar imaging (EPI) readout to acquire the magnetic resonance data generated in response to applying the at least one RF saturation pulse by sampling in each of a plurality of repetition time periods a first gradient echo pulse train at a first echo time, a second gradient echo pulse train in a second echo time, a first spin echo train at a third echo time, and a second spin echo at a fourth echo train. The magnetic resonance data sampled at the first echo time, the second echo time, the third echo time, and the fourth echo time may then be used to compute one or more relaxometry measurement. The relaxometry measurement may then be used to generating an oxygen-weighted image based on the one or more relaxometry measurement, and generate a pH-weighted image based on the magnetic resonance data sampled at one or more of the gradient echo times and spin echo times.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 15 is a graph that illustrates median R'2 measurements in normal appearing white matter (NAWM) and the T2 hyperintense lesions in all patients, independent of tumor grade.

FIG. 16 is a graph that illustrates median R'2 in t2 hyperintense regions for different tumor grades.

FIG. 17 is a graph that illustrates median R'2 in different brain regions for patients with glioblastoma (GBM).

FIG. 18 is a graph that illustrates median $MTR_{asym}$ at 3 ppm (%) in NAWM and T2 hyperintense lesions in all patients pooled across all tumor grades.

FIG. 19 is a graph that illustrates median $MTR_{asym}$ at 3 ppm (%) in t2 hyperintense regions for different tumor grades.

FIG. 20 is a graph that illustrates median $MTR_{asym}$ at 3 ppm (%) in different tissue types in GB.

DETAILED DESCRIPTION

Figure 1:
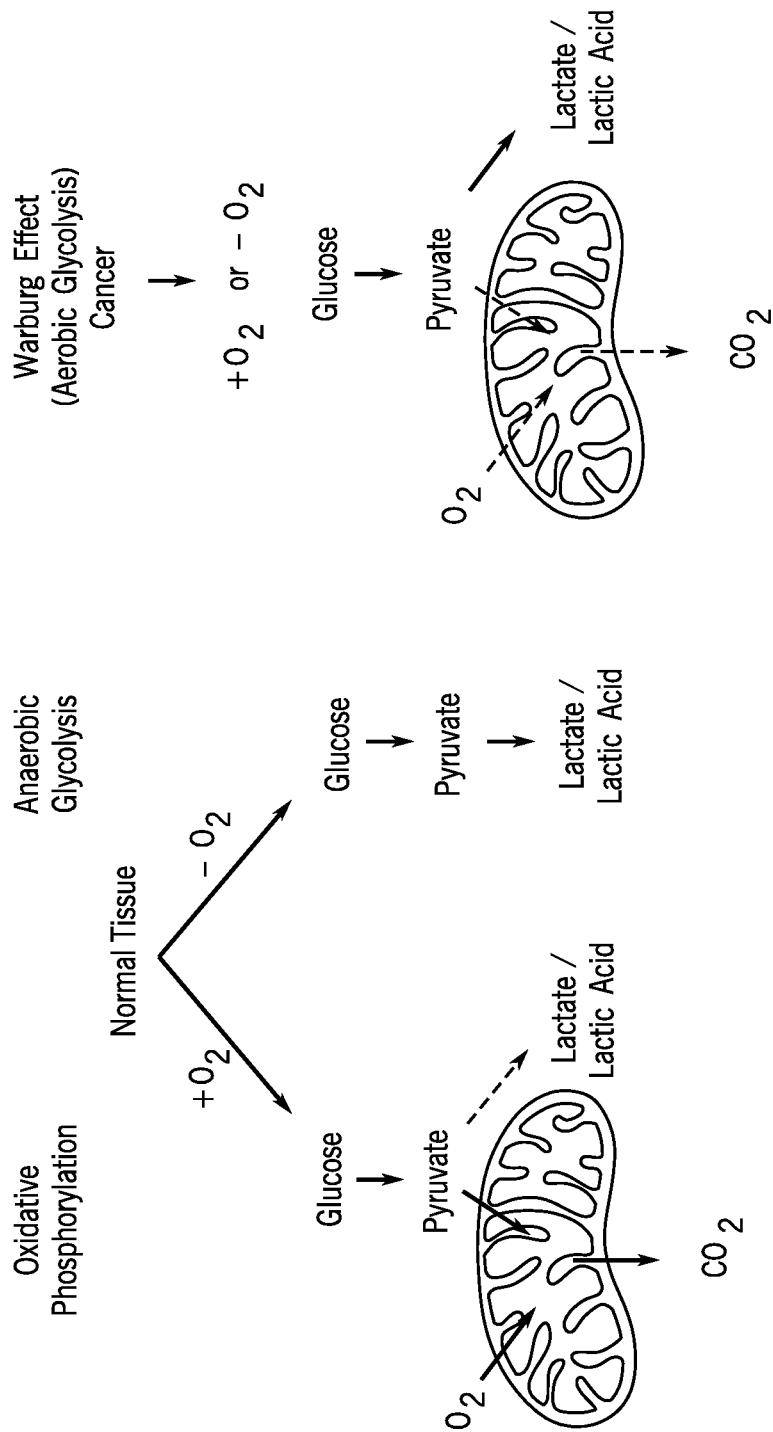
FIG. 1 is a schematic illustration of the Warburg effect. For normal tissues in the presence of oxygen, glucose is converted to pyruvate and then used for oxydative phosphorylation within the mitochondria. In normal tissues within a hypoxic environment, glucose is converted to pyruvate, then to lactate or lactic acid, decreasing extracellular pH. In cancer cells, glucose is converted to pyruvate then to lactate and lactic acid (80-85%) and a small portion of pyruvate enters the citric acid cycle (5-15%), regardless of whether oxygen is present. This altered metabolism, also known as the Warburg effect or aerobic glycolysis, results in increased extracellular acidity (lower pH) even when tumor tissue is well perfused.

The MR or NMR signals acquired with an MRI system are signal samples of the subject of the examination in Fourier space, or what is often referred to in the art as "k-space." The MR or NMR signals can be used to measure the exchange of magnetization between molecules to provide unique information about the chemical and molecular environment of samples or tissues. One type of such exchange measurement is broadly referred to in the field as magnetization transfer. This technique is capable of measuring the exchange of magnetization from spin species that have short transverse relaxation times ($T_2$). Because many different molecules have a short $T_2$, this technique is not particularly specific.

A second type of magnetization exchange occurs between water protons and a molecule with long enough T that its difference in frequency from water can be observed. Saturation of the magnetization from this molecule will generally decrease the measurable signal from water. This effect is generally referred to in the field as chemical exchange saturation transfer ("CEST"). Two different types of molecules can generate CEST effects: endogenous, or naturally occurring, molecules and exogenous contrast agents. In either instance, the molecules whose chemical exchange with water produces the CEST effect are generally referred to as so-called "exchangeable protons."

The CEST imaging method offers three advantages over traditional molecular MRI techniques. First, in some cases the molecules of interest within the subject can be directly detected. This feature mitigates the need for administering contrast agents to the subject. Second, the image contrast mechanism can be controlled with the RF pulses produced by the MRI system and, as such, can be turned on and off when desired. This control allows the location of specific molecules of interest to be detected by comparing images having the desired contrast present to those where it has been turned off. Lastly, the CEST imaging method is far more sensitive than traditional molecular MRI techniques, making it able to detect substantially low concentrations of given molecules.

Measuring the exchange of magnetization between molecules with nuclear magnetic resonance can provide unique information about the chemical and molecular environment of samples or tissues. CEST imaging renders MRI, which usually detects only bulk water signal, sensitive to metabolites and their byproducts, such as glucose and lactate. The CEST imaging method is built upon the method of conventional magnetization transfer. The CEST contrast is achieved by the selective irradiation of labile protons, which in turn attenuate the bulk water signal through saturation transfer. Labile protons are saturated using either an off-resonance pulse or continuous wave of RF irradiation. This saturation process is known as "RF labeling" or simply "labeling". It is the transfer of this saturation through chemical exchanges between the exchangeable and water protons that forms the basis of CEST imaging methods.

In particular, frequency-dependent saturation effects are visualized similar to conventional magnetization transfer (MT) spectra by plotting the water saturation, often normalized by the signal without saturation, as a function of saturation frequency. This gives what has been dubbed a "Z spectrum" or the "CEST spectrum."

The size of the CEST effect is determined by how quickly the protons exchange their magnetization with water. This exchange rate is believed to be determined by pH, so the CEST effect can also potentially provide information indicative of altered pH levels. The chemical exchange between bulk water and amide protons from endogenous proteins and peptides has been shown to be sensitive to ischemic tissue acidosis, and as a result has given rise to an imaging technique referred to as amide proton transfer (APT) imaging. Since tissue pH decreases (e.g., becomes acidic) in response to abnormal glucose/oxygen metabolism during acute ischemia, pH-sensitive APT imaging may serve as a surrogate metabolic imaging marker for stroke. In that it complements perfusion and diffusion MRI, APT imaging may allow better characterization of penumbra for predicting ischemic tissue outcome in acute stroke.

In addition to glucose, glutamine is also a major source of fuel for malignant tumors. It is essential for cellular proliferation, tumor growth, and tumor cell survival. Glutamine is the most abundant amino acid in the body, circulating at concentrations of 0.6 to 0.9 mM and as high as 20 mM in tissue. Tumor cells often consume a significant amount of glutamine, acting at times like a "glutamine trap." Glutamine demand is so high that transport systems are amplified to increase glutamine consumption. Glutamine has 2 nitrogen functional groups, an amine and an amide group, having hydrogen NMR resonance frequencies of 3.0 and 3.5 ppm, respectively, compared with water protons. The chemical exchange between amine and amide protons in bulk water is pH dependent using CEST imaging techniques. The inherently elevated concentration of glutamine within tumors further increases the available proton exchange, resulting in a higher CEST signal at 3.0 ppm. The combination of increased protons (low pH) and increased glutamine makes pH-weighted MRI using CEST contrast from amine protons on glutamine particularly attractive as a noninvasive tool for assessment of microenvironment acidity, especially for regions with elevated amine proton concentrations such as malignant brain tumors.

Figure 2A:
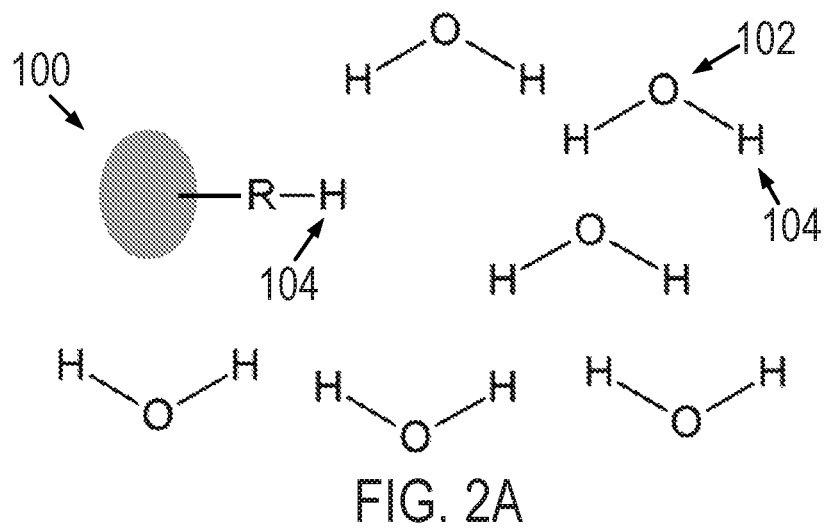
FIG. 2A is a schematic illustration of a small quantity of metabolite dissolved in a solvent, where each of the metabolite and the solvent include exchangeable protons in chemical exchange.
Figure 2B:
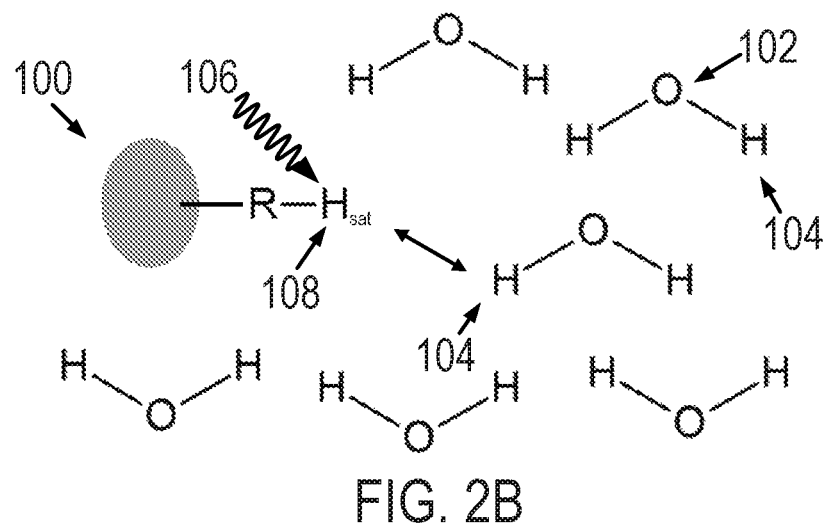
FIG. 2B is a schematic illustration of an RF pulse being applied to the exchangeable proton on the metabolite to form a saturated proton, where the saturated proton is in chemical exchange with the solvent.
Figure 2C:
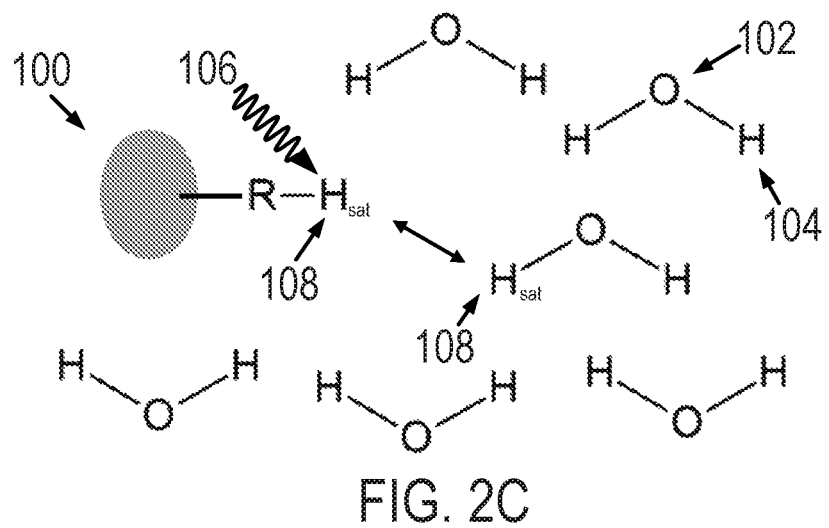
FIG. 2C is a schematic illustration of the saturated proton being transferred to the solvent resulting in a loss of solvent signal over time.

Referring now to FIGS. 2A-2C, a schematic illustration is shown to illustrate magnetization transfer via chemical exchange between a metabolite and a bulk solvent solution, which is exploited to achieve CEST contrast. FIG. 2A shows a metabolite 100 dissolved in a solvent 102 where both the metabolite 100 and the solvent 102 comprise an exchangeable proton 104. FIG. 2B shows an exchangeable proton 104 being selectively saturated by an RF pulse 106 to produce a saturated proton 108. Magnetic saturation will spontaneously be transferred to the solvent 102 overtime due to chemical exchange/through space magnetization transfer of the saturated proton 108 with the exchangeable protons 104, as shown in FIG. 2C. This process continues to produce a reduction in the solvent 102 signal over time, which may be detected using MR imaging. The loss of solvent 102 signal provides an indirect measure for the concentration of the metabolite 100 in the solution, which may be visualized from the variation in the solvent 102 signal as a function of offset frequency of the irradiation pulse, known as a Z-spectrum. CEST imaging has been demonstrated in mapping low-concentration endogenous metabolites 100 with exchangeable protons 104 such as metabolites 100 with amide (—NH), amine (NH$_2$) and hydroxyl (—OH) functional groups. Typically, the solvent 102 comprises water, but could conceivably be any solvent 102 that includes an exchangeable proton 104.

Figure 3A:
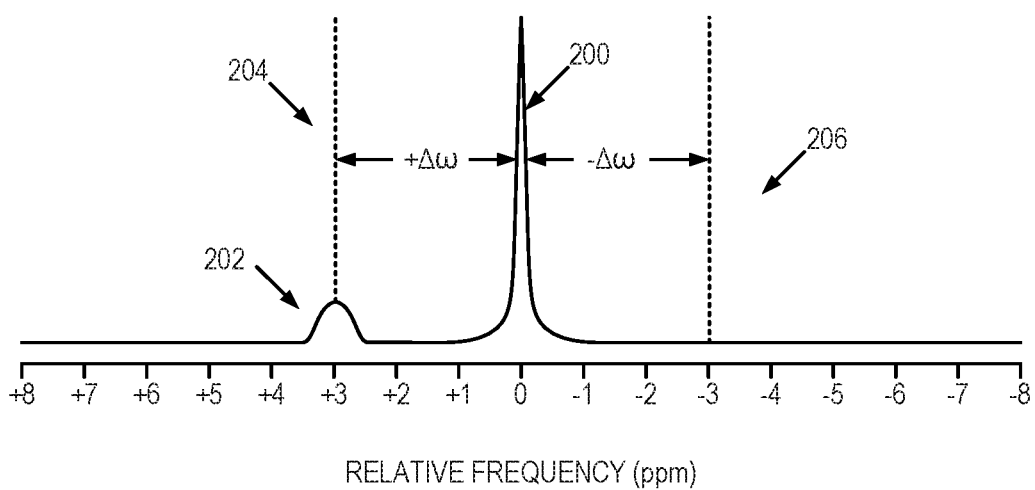
FIG. 3A is a graphic illustrations of an exemplary frequency spectrum that includes a water proton resonance peak and an amide proton resonance peak, which is only one specific example of the more general group of other labile protons groups and semisolid macromolecules.
Figure 3B:
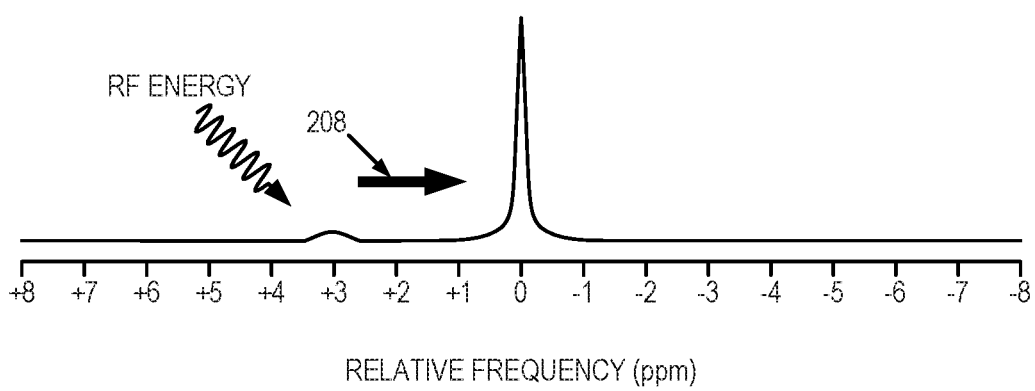
FIG. 3B is a graphic illustration of the effect of the application of radio frequency ("RF") energy at a labeling frequency that is around the resonance frequency of an exchangeable proton, such as an amide proton, on detectable signal from water protons adjacent the exchangeable proton.
Figure 3C:
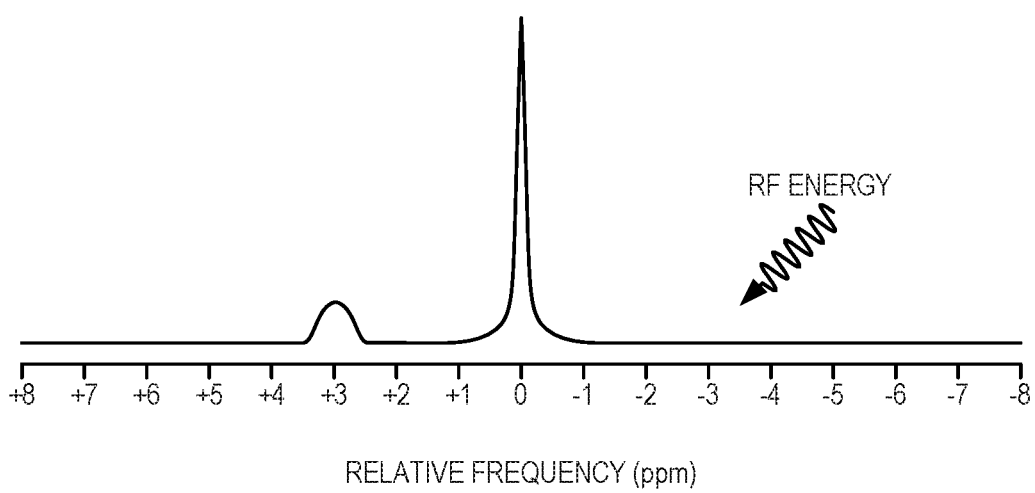
FIG. 3C is a graphic illustration of the effect of the application of RF energy at a reference frequency, equal to the negative of the labeling frequency, on detectable signal from water protons adjacent the exchangeable proton.

As suggested, CEST MRI is a sensitive imaging technique for detecting compounds containing exchangeable protons. Such labile protons can be selectively saturated by an RF pulse, and the saturation subsequently transferred to the bulk water signal via proton chemical exchange, resulting in substantial sensitivity enhancement. Referring now to FIGS. 3A-3C, a graphic illustration of an exemplary method for producing a CEST Z spectrum is shown. An exemplary Z spectrum is illustrated in FIG. 3A, where the spectrum includes a spectral peak 200 corresponding to water protons and a spectral peak 202 corresponding to amine protons. The amine proton peak 202 exists at a frequency shift relative to the water peak 200. For example, there is a frequency shift of around +3.0 parts per million ("ppm") between the water peak 200 and the amine proton peak 102. Thus, a so-called "labeling spectral line" 204, or "labeling frequency," is centered at or around the resonance frequency of the exchangeable proton, which for an amine proton is shifted about +3.0 ppm relative to the water peak 200. In general, for CEST imaging, the labeling spectral line is selected as a frequency at or around the resonance frequency of the exchangeable proton. A so-called "reference spectral line" 206, or "reference frequency," also exists, and is equal to the negative of the labeling frequency relative to the water peak 200.

To obtain a Z-spectrum, a series of image data are acquired with an MRI system by applying RF energy at the labeling spectral line changing incrementally, for example from down-field 204 to up-field 206 of water resonance. If the labeling spectral line is applied at the resonance frequency of the exchangeable proton, the saturation of the exchangeable protons is transferred through chemical exchange processes to nearby water protons, as indicated by line 208 in FIG. 3B. As a result, the detectable signal from these water protons is reduced. Referring now to FIG. 3C, there is no saturation transferred to the adjacent water spins and, therefore, no resultant decrease in detectable signal. In this manner, a so-called "Z spectrum" is acquired.

Referring back to FIG. 1, the Warburg effect also suggests that the level of glycolysis in a tissue depends on both the accumulation of lactic acid and the inefficient use of oxygen. Thus, image maps that are sensitive to tumor oxygen metabolism may be another useful noninvasive imaging technique used for understanding the relative level of aerobic (pathologic) versus anaerobic (normal) glycolysis. Blood oxygen level-dependent imaging allows for noninvasive estimation of blood or tissue oxygenation (e.g., oxygen metabolism) by estimating the concentration of deoxyhemoglobin in the region of interest. Simply stated, oxygenated blood containing oxyhemoglobin is diamagnetic, as the iron at the core is magnetically shielded from blood water, resulting in coherent MR spins and a high MR signal. In deoxygenated blood, the iron is exposed to blood water, resulting in magnetic interference with the proton magnetic moment on water molecules. This interference results in incoherent MR spins and signal dropout in the areas of high deoxyhemoglobin concentration. The paramagnetic nature of deoxyhemoglobin enhances the effective transverse relaxation rate R*. Changes in tissue R* therefore reflect relative changes in concentration of deoxyhemoglobin, and thus provides an indirect measure of oxygen extraction fraction (OEF).

Use of the reversible transverse relaxation rate, $R'2=R^*_2-R_2$, both isolates the local susceptibility effect while compensating for $R_2$ changes from factors such as water content variation. In some aspects, the sensitivity of $R'_2$ to concentration of deoxyhemoglobin may correlate with the hypoxic state of the tissue. In general, $R'_2$ does not allow for a direct measurement of OEF; however, OEF is proportional to $R'_2$ after normalization to relative blood volume fraction and static dephasing, which is expected for protons in blood at the specific magnetic field strength. This approach may be used to track oxygen metabolism within a region-of-interest, such as in brain tumors, as well as stroke. Although higher measures of $R^*_2$ may suggest higher concentration of deoxyhemoglobin, OEF, and/or local hypoxia, many other biological and/or technical influences (e.g., B1 homogeneity) may influence this measurement.

In general, the present disclosure provides a method for generating fast, non-invasive, and high resolution pH-sensitive and oxygen-sensitive contrast maps by using a MRI pulse sequence herein referred to as chemical exchange saturation transfer (CEST) spin-and-gradient echo (SAGE) echo-planar imaging (EPI), or (CEST-SAGE-EPI). Advantageously, the CEST-SAGE-EPI technique may simultaneously produce pH-weighted and oxygen-weighted image contrasts for evaluation of tissue microenvironments.

Unlike conventional CEST imaging techniques and BOLD imaging techniques that would require two separate and distinct pulse sequences to produce a pH map and an oxygen map for a desired tissue, the CEST-SAGE-EPI technique may drastically reduce scan time requirements by simultaneously producing a pH-weighted image and an oxygen-weighted image using one or more repetition time period (TR) within the same pulse sequence. Furthermore, in comparison to conventional gradient echo readouts that generate ~1 to 3 slices in 10 minutes, the CEST-SAGE-EPI technique may simultaneously produce high resolution pH-weighted and oxygen-weighted contrast images within clinically feasible scan times, for example, at or below approximately 7 minutes. Other advantages of the CEST-SAGE-EPI technique will become apparent through the description below.

In general, the methods described in the present disclosure include applying at least one radiofrequency (RF) saturation pulse at a frequency or a range of frequencies to substantially saturate magnetization corresponding to an exchangeable proton in the region of interest to generate magnetic resonance data. The magnetic resonance data generated in response to the RF saturation pulse is then acquired by performing an echo-planar imaging (EPI) readout. In some aspects, the EPI readout is configured to acquire the magnetic resonance data by sampling a series of gradient echo pulse trains at a series of gradient echo times and sampling a series of spin echo pulse trains at a series of spin echo times. For example, the EPI readout may be configured to acquire the magnetic resonance data in each of a series of repetition time periods a first gradient echo pulse train at a first echo time, a second gradient echo pulse train at a second echo time, a first spin echo pulse train at a third echo time, and a second spin echo train at a fourth echo time. One or more relaxometry measurement is then computed using the magnetic resonance data. For example, data sampled from the first echo time, the second echo time, the third echo time, and the fourth echo time may be used to compute the one or more relaxometry measurement. A oxygen-weighted image may then be generated based on the one or more relaxometry measurement, and a pH-weighted image may be generated using sampled magnetic resonance data at one or more of the gradient echo times or spin echo times. For example, the pH-weighted image may be generated using one or more of the first echo time, the second echo time, the third echo time, and the fourth echo time.

Mathematically, the theory of measurement may be explained, without limiting the disclosure, as follows:

Measurement pH-Sensitive and Oxygen-Sensitive Contrast Maps:

The magnetization of bulk water protons undergoing chemical exchange with exchangeable protons (e.g., amine protons) can be described by the Bloch-McConnell equations in the form of:

$$\frac{dM(t)}{dt} = X \cdot M(t) - c \tag{1}$$

where, $$M = \begin{pmatrix} M_{ax} \\ M_{bx} \\ M_{ay} \\ M_{by} \\ M_{az} \\ M_{bz} \end{pmatrix}, X = \begin{pmatrix} M_{ax} & k_b & -\delta a & 0 & 0 & 0 \\ M_{bx} & C_{2b} & 0 & -\delta b & 0 & 0 \\ M_{ay} & 0 & C_{2a} & k_b & -\omega_1 & 0 \\ M_{by} & \delta b & k_a & C_{2b} & 0 & -\omega_1 \\ M_{az} & 0 & \omega_1 & 0 & C_{1a} & k_b \\ M_{bz} & 0 & 0 & \omega_1 & k_a & C_{1b} \end{pmatrix}, \tag{2}$$

$$c = \begin{pmatrix} M_{ax} \\ M_{bx} \\ M_{ay} \\ M_{by} \\ M_{az} \\ M_{bz} \end{pmatrix};$$

where pool a and pool b are the bulk water protons and an exchangeable proton (e.g., amine protons), respectively; $M_{a z0}$ and $M_{b z0}$ are the equilibrium magnetizations of pool a and pool b, respectively; $k_b$ is the exchange rate of protons from pool b to pool a; $k_a$ is the exchange rate of protons from pool a to pool b as given by $(M_{b0}/M_{a0}) \cdot k_b$; $\omega_1$ is the RF pulse amplitude as given by $\omega_1 = \gamma \beta_1(t)$, where $\gamma$ is the gyromagnetic ratio and $\beta_1(t)$ is given in $\mu T$; $\delta_a = \omega - \omega_a$ and $\delta_b = \omega - \omega_b$ where $\omega$ is a applied RF irradiation frequency, $\omega_a$ is the bulk water resonance frequency, and $\omega_b$ is the exchangeable proton frequency (e.g., amine proton resonance frequency); $T_{1a}$ and $T_{1b}$ are the longitudinal relaxation times of pool a and pool b, respectively; and $$C_{1a} = \left(\frac{1}{T1a}\right) + k_a, \ C_{2a} = \left(\frac{1}{T2a}\right) + k_a, \ C_{1b} = \left(\frac{1}{T1b}\right) + k_b,$$

$$C_{2b} = \left(\frac{1}{T2b}\right) + k_b$$

represent the sum of exchange and relaxation rates. Equation 1 can be solved in a number of ways, for example, Equation 1 can be solved analytically to yield:

$$M(t) = e^{Xt} \cdot M_0(X/c) - (X/c) \tag{3}$$

where $M_{az}(t)$ represents the longitudinal magnetization of bulk water available for subsequent readout after CEST effects. Assuming the spoiler duration and water excitation pulse duration are negligible, $M_{az}(t)$ immediately following excitation reflects the available longitudinal magnetization for subsequent readout. The chemical exchange between the exchangeable proton (e.g., amine protons) and bulk water protons can be characterized as a base-catalyzed process, governed by pH as follows:

$$k_b = k_0 + k_{base} * 10^{-(14-pH)} \quad (4)$$

where $k_0$ is the default exchange rate; $k_{base}$ is the base-catalyzed rate constant; and $k_b$ is the exchange rate of protons from the metabolite proton pool to the water pool. In some aspects, $k_0$ and $k_{base}$ were estimated to be 76 and 5.6 Hz, respectively, using glutamine phantoms with a concentration of 50 mM.

During the CEST imaging experiment, the RF saturation frequency ($\omega$) is swept over a range of values to obtain a z-spectral data set, as described above. To reduce the effects of T1 and T2 weighting, along with other confounding effects, the attenuation of bulk water magnetization following a saturation pulse is described by the MTR given by:

$$MTR(\omega) = S(\omega)/S_0 \quad (5)$$

where $S(\omega)$ is the amount of bulk water signal available after the saturation pulse with frequency $\omega$; and $S_0$ is the signal available without application of RF saturation. Because MTR can be affected by symmetric effects of direct water saturation and conventional magnetization transfer effects, CEST contrast is often described by the asymmetry in the magnetization transfer ratio ($MTR_{asym}$) with respect to water proton resonance, as follows:

$$MTR_{asym}(\omega) = \frac{S(-\omega) - S(\omega)}{S_0} \quad (6)$$

As one non-limiting example, for amine proton CEST imaging the $MTR_{asym}$ is evaluated at 3.0 ppm with respect to the bulk water resonance frequency. In some aspects, following acquisition the CSET data may be processed using motion corrections (e.g., mcflirt; FSL, FMRIB, Oxford, UK), and $B_0$ correction using any number of techniques, such as a WASSR method. This may include interpolating the data points around 0 ppm and shifting the CEST spectra so that the lowest value of the curve is set to 0 ppm.

Estimates of $R'_2$ were achieved through use of a SAGE-EPI readout that, in some aspects, includes 2 gradient echoes (TE1 and TE2), an asymmetric spin echo (TE3), and a spin-echo (TE4) EPI acquisition during a single excitation event. The solutions for $R^*_2$ and $R_2$ using the SAGE EPI may be described as:

$$A = Y^{-1}S \quad (7)$$

where, $$S = \begin{pmatrix} \ln(S_1) \\ \ln(S_2) \\ \ln(S_3) \\ \ln(S_4) \end{pmatrix}, Y = \begin{pmatrix} 1 & 0 & -TE_1 & 0 \\ 1 & 0 & -TE_2 & 0 \\ 1 & -1 & -TE_4 + TE_3 & TE_4 - 2 \cdot TE_3 \\ 1 & -1 & 0 & -TE_4 \end{pmatrix}. \quad (8)$$

$$A = \begin{pmatrix} \ln(S_0) \\ \ln(\delta) \\ R^*_2 \\ R_2 \end{pmatrix};$$

where $S_n$ is the signal magnitude for the nth echo and $\delta$ is the differences in residual signal differences caused by imperfectly matched slice profiles between echo trains before and after the refocusing pulse. Finally, the gradient echoes and spin echoes of the $S_0$ image can then be fit separately to monoexponential decay functions to obtain maps of T2* and T2, respectively. This data is then used to calculate a map of R2' from the following equation:

$$R'_2 = R^*_2 - R_2 = \frac{1}{T^*_2} - \frac{1}{T_2} \quad (9)$$

where a higher value of R2' suggests relatively higher concentrations of hemoglobin, oxygen extraction fraction, and/or hypoxia. The R2' map can also be combined with standard cerebral blood flow (rCBF) and cerebral blood volume (rCBV) data acquired using a separate perfusion sequence to obtain maps of relative oxygen extraction fraction (rOEF) and relative cerebral metabolic rate of oxygen (rCMRO2). The relative oxygen extraction fraction (rOEF) is a parameter that describes the fraction of deoxygenated blood, which in the case of fully saturated arterial blood is calculated as:

$$rOEF = \frac{R'_2}{C * rCBV} \quad (10)$$

where $C = 3/4\pi\gamma\Delta\chi B_0$, with the gyromagnetic ratio $\gamma = 42.57*10^6$ Hz/T, the susceptibility difference between fully deoxygenated and fully oxygenated blood $\Delta\chi = 9.24*10^{-7}$, and magnetic field strength $B_0$. The relative cerebral metabolic rate of oxygen (rCMRO$_2$), a measure describing the rate of oxygen metabolism, was calculated as:

$$rCMRO_2 = rCBF * rOEF \quad (11)$$

where a high value of rCMRO$_2$ is suggestive of high oxygen metabolism.

Figure 4:
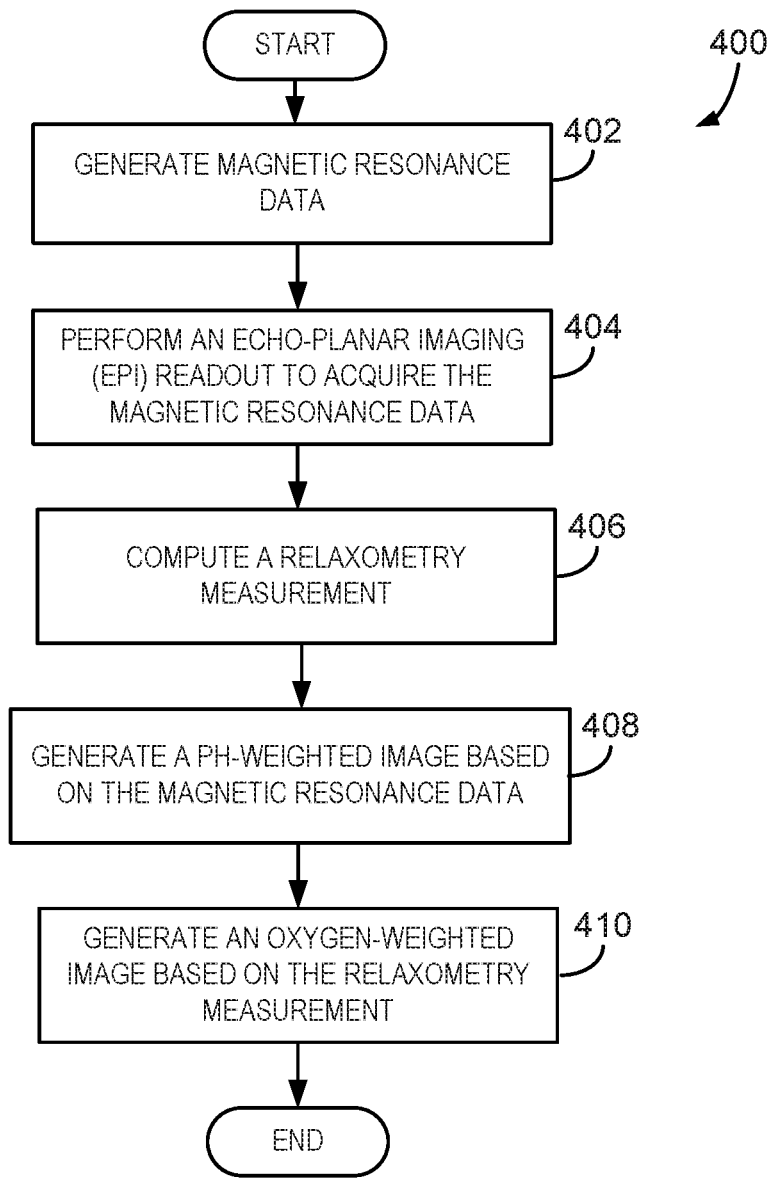
FIG. 4 is a flowchart illustrating one non-liming example of a CEST imaging technique in accordance with the present disclosure.

Referring now to FIG. 4, a flowchart is illustrated as setting forth the steps of an example method 400 for producing pH-sensitive and oxygen-sensitive magnetic resonance (MR) images in a region of interest of a subject using the CEST-SAGE-EPI technique. In one aspect, the method 400 includes applying at least one radiofrequency (RF) saturation pulse at a frequency or a range of frequencies to substantially saturate magnetization corresponding to an exchangeable proton in the region of interest to generate magnetic resonance data, as indicated at step 402. The magnetic resonance data generated in response to the RF saturation pulse is then acquired by performing an echo-planar imaging (EPI) readout, as indicated at step 404. In some aspects, the EPI readout is configured to acquire the magnetic resonance data by sampling a series of gradient echo pulse trains at a series of gradient echo times and by sampling a series of spin echo pulse trains at a series of spin echo times. In one aspect, the EPI readout is configured to acquire the magnetic resonance data by sampling, in each of a series of repetition time periods, a first gradient echo pulse train at a first echo time, a second gradient echo pulse train at a second echo time, a first spin echo pulse train at a third echo time, and a second spin echo train at a fourth echo time.

The magnetic resonance data acquired using the EPI readout may then be processed to compute one or more relaxometry measurement, as indicated at step 406. The one or more relaxometry measurement may be computed using the first echo time, the second echo time, the third echo time, and the fourth echo time. For example, the one or more relaxometry measurement may be computed using Equations (8) and (9).

As indicated at step 408, a pH-weighted image is then generated using the magnetic resonance data, which may be indicative of the concentration of the exchangeable proton in the region of interest. The pH-weighted image may be generated using magnetic resonance data obtained from one or more of the gradient echo times or spin echo times. For example, the data sampled from one or more of the first echo time, second echo time, third echo time, and/or fourth echo time may be used to generate the pH-weighted image. In some aspects, it is may be advantageous to average the signal between one or more of the echo times to reduce signal to noise while generating the pH-weighted image, for example, average the signals sampled from the first echo time and the second echo time. In some aspects, the magnetic resonance data includes chemical exchange saturation transfer (CEST) data. For example, the CEST data may include the magnetization of bulk water protons undergoing chemical exchange with exchangeable protons (e.g., amine protons), which may be determined using Equations (1)-(4).

The CEST data may be used to obtain a z-spectra data set. To reduce the confounding effects, the CEST contrast may be modeled using asymmetry in the magnetization transfer ratio ($MTR_{asym}$), as described in Equations (5)-(6). In some aspects, the pH-weighted image includes a contrast map of the magnetization transfer ratio corresponding to an exchangeable proton within the region of interest. For example, the CEST-SAGE-EPI sequence may be configured to apply the at least one RF saturation pulse at the range of frequencies corresponding to an amine exchangeable proton to generate the magnetization transfer ratio (e.g., $MTR_{asym}$ at 3.0 ppm), as described above. In some aspects, the signal to noise ratio of the resulting $MTR_{asym}$ measurement/image may be reduced by taking an average of the magnetic resonance data at the first echo time and the second echo time.

Other suitable techniques for generating the pH-weighted image may include, but are not limited to, chemical exchange rotation transfer techniques, Lorentzian difference analysis, multiple-pool Lorentzian fitting, and the 3-point method. In some aspects, following acquisition the magnetic resonance data may be processed using motion correction (e.g., a mcflirt technique) and $B_0$ corrections (e.g., a WASSR method).

An oxygen-weighted image may then be generated using the one or more relaxometry measurement, as indicated at step 410. In some aspects, the oxygen-weighted image is indicative of a concentration of deoxyhemoglobin within the region of interest. In some aspects, the oxygen-weighted image may comprise a contrast map of the reversible transverse relaxation rate ($R'_2$) over the region of interest. In other aspects, the oxygen-weighted image may comprise a relative oxygen extraction fraction or a relative cerebral metabolic rate of oxygen as described in Equations (10) and (11). In some aspects, the oxygen-weighted image and the pH-weighted image are generated simultaneously.

The pH-weighted and oxygen-weighted maps are useful in a number of clinical applications. For example, the pH-weighted and oxygen-weighted image maps may be used to assist a physician in diagnosing or identifying tissue affected by an ischemic injury or a traumatic injury that includes micro- or macroscopic bleeds. In some aspects, a suspected ischemic region of a subject may be imaged using the method 400 such that the pH-weighted image is generated to exhibit a positive contrast for ischemic regions, and wherein the oxygen-weighted image is configured to display a negative contrast for ischemic regions. Similar, a suspected traumatic injury that includes micro- or macroscopic bleeding may be imaged such that the pH-weighted image is generated to exhibit a negative contrast for regions that include micro- or macroscopic bleeding, and wherein the oxygen-weighted image is configured to display a positive contrast for regions that include micro- or macroscopic bleeding.

The method 400 may be useful in assisting a physician to diagnose or identify a number of primary injuries that include, but are not limited to, cerebral contusions, blood vessel damage, axonal shearing, blood brain barrier damage, and nerve apoptosis. The method 400 may further be useful in assisting a physician to diagnose or identify a number of secondary injuries that include, but are not limited to, ischemia, hypoxia, cerebral edema, ICP elevation, acidosis, neurotransmitters release, and free radical formation.

Figure 5:
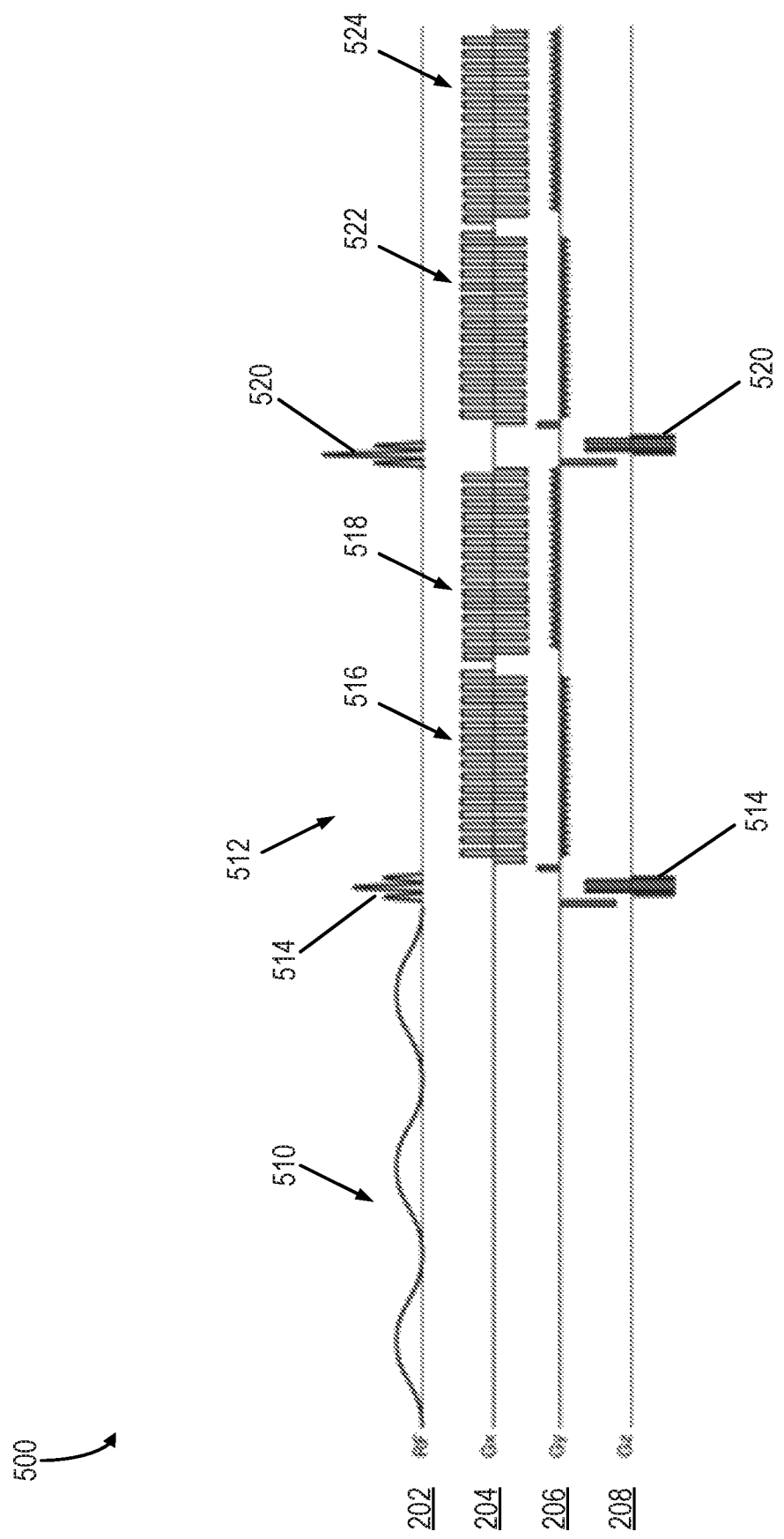
FIG. 5 is a non-limiting example of a multi-echo CEST spin-and-gradient echo (CEST-SAGE-EPI) sequence in accordance with the present disclosure.

Referring to FIG. 5 a non-limiting example method for employing the CEST-SAGE-EPI technique 500 is illustrated according to one aspect of the present disclosure. In general, the method 500 includes applying at least one radiofrequency (RF) saturation pulse at a frequency or a range of frequencies to substantially saturate magnetization corresponding to an exchangeable proton in the region of interest to generate magnetic resonance data. The at least one RF saturation pulse may include an off-resonance CEST excitation RF pulse 510 and a spectral-spatial water only excitation 514. In some aspects, the off-resonance CEST excitation RF pulse 510 includes a train of three Gaussian pulses. In one non-limiting example, the RF saturation pulse 510 comprises three Gaussian pulses applied for approximately 100 ms and at an amplitude of approximately 6 uT.

Following excitation, an echo-planar imaging (EPI) readout 512 is performed to acquire the magnetic resonance data generated in response to applying the at least one RF saturation pulse by sampling in each of a plurality of repetition time periods a series of gradient echo times by sampling a series of gradient echo pulse trains and a series of spin echo times by sampling a series of spin echo pulse trains. In one non-limiting example the method 500 includes a first gradient echo pulse train 516 configured to sample at a first echo time, a second gradient echo pulse train 518 configured to sample a second echo time, a first spin echo train 522 configured to sample a third echo time, and a second spin echo 524 configured to sample a fourth echo train. In some aspects, a refocusing pulse is configured between the series of gradient echo pulse trains and the series of spin echo pulse trains. Suitable refocusing pulses may comprise a 180 degree refocusing pulse. In some aspects, the first spin echo includes an asymmetric spin echo pulse train.

Figure 6:
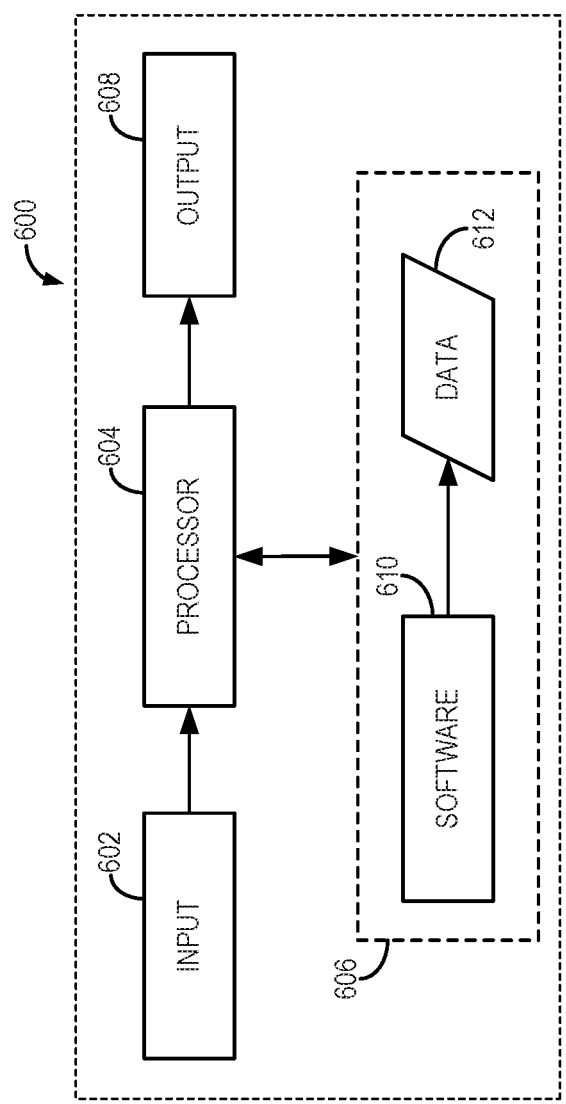
FIG. 6 is a block diagram illustrating an example of a computer system that can implement some embodiments of the present invention.

Referring now to FIG. 6, a block diagram of an example of a computer system 600 that can perform the methods described in the present disclosure is shown. The computer system 600 generally includes an input 602, at least one hardware processor 604, a memory 606, and an output 608. Thus, the computer system 600 is generally implemented with a hardware processor 604 and a memory 606.

In some embodiments, the computer system 600 can be implemented, in some examples, by a workstation, a notebook computer, a tablet device, a mobile device, a multimedia device, a network server, a mainframe, one or more controllers, one or more microcontrollers, or any other general-purpose or application-specific computing device.

The computer system 600 may operate autonomously or semi-autonomously, or may read executable software instructions from the memory 606 or a computer-readable medium (e.g., a hard drive, a CD-ROM, flash memory), or may receive instructions via the input 602 from a user, or any another source logically connected to a computer or device, such as another networked computer or server. Thus, in some embodiments, the computer system 600 can also include any suitable device for reading computer-readable storage media.

In general, the computer system 600 is programmed or otherwise configured to implement the methods and algorithms described in the present disclosure, such as those described in FIGS. 2-5. For instance, the computer system 600 can be programmed to produce pH-sensitive and oxygen-sensitive magnetic resonance images from an acquired MRI signal, as described above. In some aspects, the computer system 600 may be programmed to access acquired data from an MRI system, such as the magnetic resonance data 404 and/or the one or more relaxometry measurement 406. Alternatively, the magnetic resonance data 404 and/or the one or more relaxometry measurement 406 may be provided to the computer system 600 by acquiring the data using an MRI system and communicating the acquired data to the computer system, which may be part of the MRI system.

The computer system 600 may be further programmed to process the magnetic resonance data 404 and/or the one or more relaxometry measurement 406 to generate pH-weighted contrast images and oxygen-weighted contrast images, as described in FIGS. 2-5. The input 602 may take any suitable shape or form, as desired, for operation of the computer system 600, including the ability for selecting, entering, or otherwise specifying parameters consistent with performing tasks, processing data, or operating the computer system 600. In some aspects, the input 602 may be configured to receive data, such as data acquired with a MRI system, such as the system described in FIG. 6. Such data may be processed as described above to generate pH-weighted and oxygen-weighted contrast images. In addition, the input 602 may also be configured to receive any other data or information considered useful for determining the concentration of the contrast agent using the methods described above.

Among the processing tasks for operating the computer system 600, the one or more hardware processors 604 may also be configured to carry out any number of post-processing steps on data received by way of the input 602. For example, the processor may be configured to apply motion correction techniques or $B_0$ corrections, as described in FIGS. 2-5.

The memory 606 may contain software 610 and data 612, such as data acquired with an MRI system, and may be configured for storage and retrieval of processed information, instructions, and data to be processed by the one or more hardware processors 604. In some aspects, the software 610 may contain instructions directed to processing the magnetic resonance data 404 and/or the one or more relaxometry measurement 406 in order to compute a pH-weighted contrast image and an oxygen-weighted contrast image, as described in FIGS. 2-5. In addition, the output 608 may take any shape or form, as desired, and may be configured for displaying the images or parameters described above.

Figure 7:
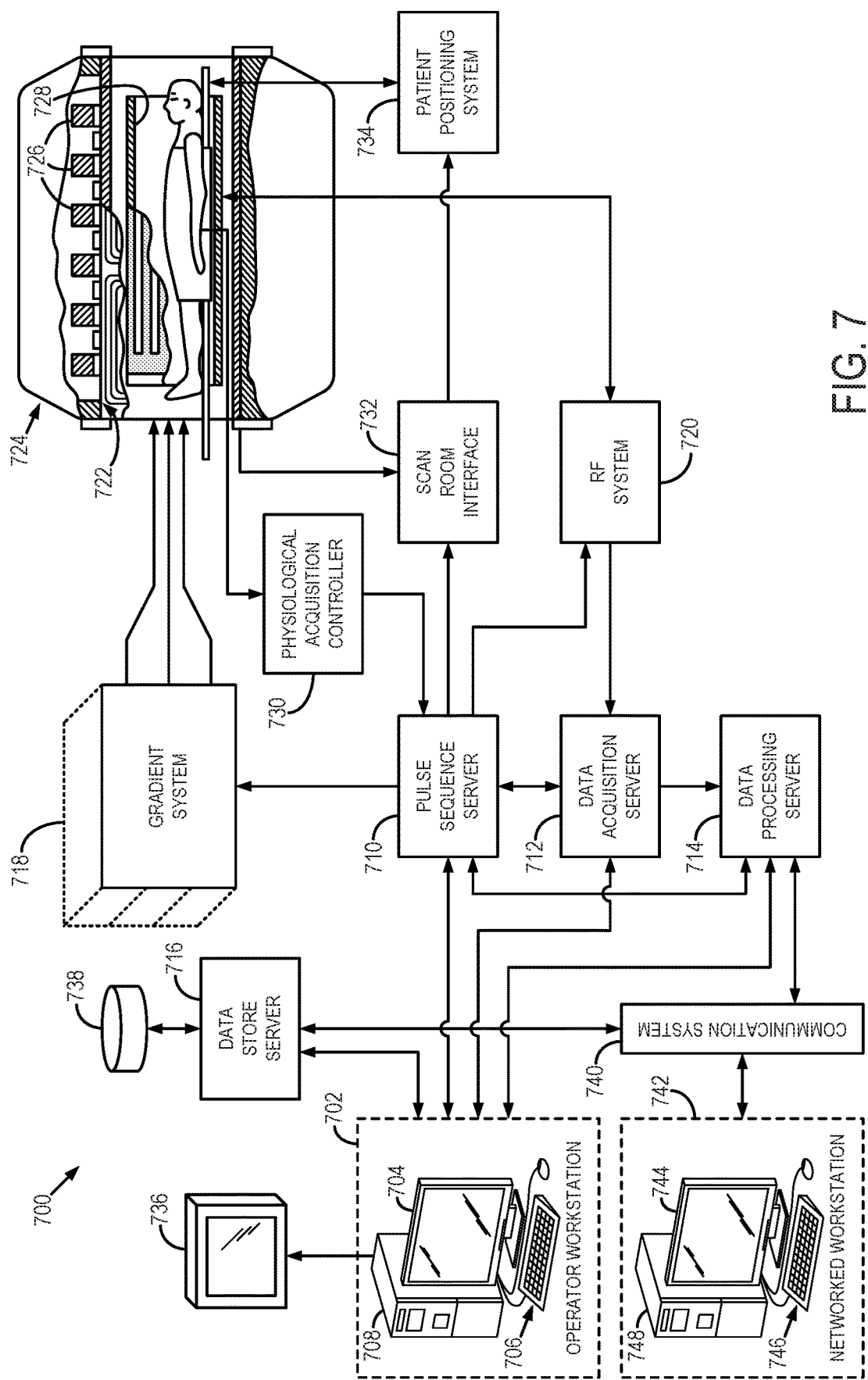
FIG. 7 is a is a block diagram of an example of a magnetic resonance imaging ("MRI") system that can implement the methods in accordance with the present disclosure.

Referring particularly now to FIG. 7, an example of an MRI system 700 that can implement the methods described here is illustrated. The MRI system 700 includes an operator workstation 702 that may include a display 704, one or more input devices 706 (e.g., a keyboard, a mouse), and a processor 708. The processor 708 may include a commercially available programmable machine running a commercially available operating system. The operator workstation 702 provides an operator interface that facilitates entering scan parameters into the MRI system 700. The operator workstation 702 may be coupled to different servers, including, for example, a pulse sequence server 710, a data acquisition server 712, a data processing server 714, and a data store server 716. The operator workstation 702 and the servers 710, 712, 714, and 716 may be connected via a communication system 740, which may include wired or wireless network connections.

The pulse sequence server 710 functions in response to instructions provided by the operator workstation 702 to operate a gradient system 718 and a radiofrequency ("RF") system 720. Gradient waveforms for performing a prescribed scan are produced and applied to the gradient system 718, which then excites gradient coils in an assembly 722 to produce the magnetic field gradients $G_x$, $G_y$, and $G_z$ that are used for spatially encoding magnetic resonance signals. The gradient coil assembly 722 forms part of a magnet assembly 724 that includes a polarizing magnet 726 and a whole-body RF coil 728.

RF waveforms are applied by the RF system 720 to the RF coil 728, or a separate local coil to perform the prescribed magnetic resonance pulse sequence. Responsive magnetic resonance signals detected by the RF coil 728, or a separate local coil, are received by the RF system 720. The responsive magnetic resonance signals may be amplified, demodulated, filtered, and digitized under direction of commands produced by the pulse sequence server 710. The RF system 720 includes an RF transmitter for producing a wide variety of RF pulses used in MRI pulse sequences. The RF transmitter is responsive to the prescribed scan and direction from the pulse sequence server 710 to produce RF pulses of the desired frequency, phase, and pulse amplitude waveform. The generated RF pulses may be applied to the whole-body RF coil 728 or to one or more local coils or coil arrays.

The RF system 720 also includes one or more RF receiver channels. An RF receiver channel includes an RF preamplifier that amplifies the magnetic resonance signal received by the coil 728 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \tag{12}$$

and the phase of the received magnetic resonance signal may also be determined according to the following relationship:

$$\varphi = \tan^{-1}\left(\frac{Q}{I}\right). \tag{13}$$

The pulse sequence server 710 may receive patient data from a physiological acquisition controller 730. By way of example, the physiological acquisition controller 730 may receive signals from a number of different sensors connected to the patient, including electrocardiograph ("ECG") signals from electrodes, or respiratory signals from a respiratory bellows or other respiratory monitoring devices. These signals may be used by the pulse sequence server 710 to synchronize, or "gate," the performance of the scan with the subject's heart beat or respiration.

The pulse sequence server 710 may also connect to a scan room interface circuit 732 that receives signals from various sensors associated with the condition of the patient and the magnet system. Through the scan room interface circuit 732, a patient positioning system 734 can receive commands to move the patient to desired positions during the scan.

The digitized magnetic resonance signal samples produced by the RF system 720 are received by the data acquisition server 712. The data acquisition server 712 operates in response to instructions downloaded from the operator workstation 702 to receive the real-time magnetic resonance data and provide buffer storage, so that data is not lost by data overrun. In some scans, the data acquisition server 712 passes the acquired magnetic resonance data to the data processor server 714. In scans that require information derived from acquired magnetic resonance data to control the further performance of the scan, the data acquisition server 712 may be programmed to produce such information and convey it to the pulse sequence server 710. For example, during pre-scans, magnetic resonance data may be acquired and used to calibrate the pulse sequence performed by the pulse sequence server 710. As another example, navigator signals may be acquired and used to adjust the operating parameters of the RF system 720 or the gradient system 718, or to control the view order in which k-space is sampled. In still another example, the data acquisition server 712 may also process magnetic resonance signals used to detect the arrival of a contrast agent in a magnetic resonance angiography ("MRA") scan. For example, the data acquisition server 712 may acquire magnetic resonance data and processes it in real-time to produce information that is used to control the scan.

The data processing server 714 receives magnetic resonance data from the data acquisition server 712 and processes the magnetic resonance data in accordance with instructions provided by the operator workstation 702. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 714 are conveyed back to the operator workstation 702 for storage. Real-time images may be stored in a data base memory cache, from which they may be output to operator display 702 or a display 736. Batch mode images or selected real time images may be stored in a host database on disc storage 738. When such images have been reconstructed and transferred to storage, the data processing server 714 may notify the data store server 716 on the operator workstation 702. The operator workstation 702 may be used by an operator to archive the images, produce films, or send the images via a network to other facilities.

The MRI system 700 may also include one or more networked workstations 742. For example, a networked workstation 742 may include a display 744, one or more input devices 746 (e.g., a keyboard, a mouse), and a processor 748. The networked workstation 742 may be located within the same facility as the operator workstation 702, or in a different facility, such as a different healthcare institution or clinic.

The networked workstation 742 may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may be exchanged between the data processing server 714 or the data store server 716 and the networked workstations 742, such that the data or images may be remotely processed by a networked workstation 742.

EXAMPLES

The following examples set forth, in detail, ways in which the present disclosure may be used or implemented, and will enable one of skill in the art to more readily understand the principles thereof. The following examples are presented by way of illustration and are not meant to be limiting in any way.

Example 1: CEST-SAGE-EPI Pulse Sequence

Simultaneous acquisition of pH-sensitive information and relaxometry measures of $R'_2$ were performed using a SAGE-EPI readout. The SAGE-EPI readout consisted of 2 gradient echoes ($TE_1$=14.0 ms; $TE_2$=34.1 ms), an asymmetric spin echo ($TE_3$=58.0 ms), and a spin echo ($TE_4$=92.4 ms). All phantom and human CEST-SAGE-EPI data were acquired with a CEST saturation pulse train consisting of 3 (3×) 100-ms Gaussian pulses with amplitude B1=6 µT, TR>10, 000 ms, FOV=240×217, matrix size=128×104, partial Fourier encoding=6/8, GRAPPA=3, bandwidth=1630 Hz/pixel, and 25 contiguous slices with a 4-mm slice thickness. A total of 29 z-spectral points were acquired with data around ±3.0 ppm and 0.0 ppm with respect to water (from −3.5 to −2.5 in intervals of 0.1; from −0.3 to +0.3 in intervals of 0.1; and from +2.5 to +3.5 in intervals of 0.1). An additional reference $S_0$ scan with identical parameters and no saturation pulse was acquired with number of excitations or averages=4. The total acquisition time for CEST-SAGE-EPI was 7 minutes and 30 seconds, benchmarked on a 3T Siemens Prisma MR scanner (Software Versions VE11A-C; Siemens Healthcare, Erlangen, Germany).

Example 2: Phantom Testing

To demonstrate the ability to simultaneously acquire pH-sensitive information along with relaxometry measures of $R_2$, $R*_2$, and $R'_2$, we performed CEST-SAGE-EPI, multi-echo gradient-echo (ME-GRE), and multi-echo spin-echo (Carr-Purcell-Meiboom-Gill [CPMG]) MR acquisition in a series of 36 glutamine phantoms (100 mM) with combinations of varying pH (5.0, 5.5, 6.0, 6.5, 7.0, 7.5) and gadopentetic acid (Gd-DTPA; Magnevist, Bayer HealthCare Pharmaceuticals, Berlin, Germany) concentration (0, 0.25, 0.5, 1.0, 1.5, and 2.0 mM) in 50-mL falcon tubes. The 100-mM glutamine solution was prepared first using distilled water. The pH in each phantom was titrated using dilute acid (0.1N HCl) and base (0.1N NaOH) solution. The desired Gd-DTPA was then added to the phantom solution and vortexed. All samples were vortexed and pH was re-evaluated prior to MRI acquisition.

The ME-GRE sequence used for $R*_2$ quantitation was collected with TE=20/40/60/80 ms, TR=10,000 ms, flip angle=90 degrees, FOV=217×240 mm, matrix size=116× 128, slice thickness=4 mm, and pixel bandwidth=260 Hz. The CPMG sequence used for $R_2$ quantitation was performed with TE=49/98/147/196/245/294/343/392 ms, TR=10,000 ms, flip angle=90 degrees, FOV=217×240 mm, matrix size=116×128, slice thickness=4 mm, and pixel band-width=260 Hz. Both the ME-GRE and CPMG sequences were repeated to improve SNR. All phantom experiments were physically repeated twice to ensure repeatability and compared with theoretical values using Bloch-McConnell simulations. Contrast-to-noise ratio (CNR) of $MTR_{asym}$ at 3 ppm between any 2 samples of differing pH a and b was calculated as:

$$CNR = \frac{|\mu_a - \mu_b|}{((\sigma_a^2 - \sigma_b^2)/2)^2} \quad (14)$$

Example 3: In Vivo Testing

A total of 47 histologically proven glioma patients (World Health Organization [WHO] IV, n=20; WHO III, n=14; WHO II, n=13) were enrolled in the current study prior to initial surgical resection or at first recurrence. All patients provided informed, written consent to have advanced imaging, and this information included in our internal review board-approved research database. In addition to CEST-SAGE-EPI prior to contrast administration, all patients received the anatomic images according to the standardized brain tumor imaging protocol, including T2-weighted fluid-attenuated inversion recovery (FLAIR) images, T2-weighted turbo spin-echo images, and diffusion-weighted images with 3-mm slice thickness and no interslice gap, along with parameter-matched, 1-mm isotropic 3D T1-weighted MPRAGE scans before and following injection of 0.01 mg/kg Gd-DTPA.

Clinical postprocessing of CEST-SAGE-EPI included affine motion correction (mcflirt; FSL, FMRIB, Oxford, United Kingdom) and B0 correction via the WASSR (water saturation shift referencing) method, and/or creating B0 maps using phase information from the 2 acquired gradient echoes. An integral of width of 0.4 ppm was then taken around both the −3.0 and +3.0 ppm (−3.2 to −2.8 and +2.8 to +3.2, respectively) spectral points of the inhomogeneity-corrected data. These data points were combined with the $S_0$ image to calculate $MTR_{asym}$ at 3.0 ppm as defined by Equation 6. Estimates of $T^*$, $T_2$, $T'_2$, $R^*_2$, $R_2$, and $R'_2$ from ME-GRE or CPMG were obtained by performing a mono-exponential fit to the gradient and spin echoes, respectively, whereas estimates of the same parameters were obtained using Equation 9.

For all data, the average $MTR_{asym}$ at 3.0 ppm calculated from the first (TE=14.0 ms) and second (TE=34.1 ms) gradient echoes were averaged to decrease increase the SNR of the resulting $MTR_{asym}$ images. The 2 gradient echoes were chosen instead of all echoes due to slightly higher variability in $MTR_{asym}$ measurements from asymmetric spin-echo and spin-echo measurements, due to the longer TE and additional signal loss from transverse relaxation. In phantom samples, regions of interest were drawn within each sample and the mean ($\mu$) and SD ($\sigma$) of $MTR_{asym}$ at 3 ppm for voxels within the sample were calculated.

When evaluating glioma patients, volumes of interest were drawn within normal-appearing white matter (NAWM) contralateral to the hemisphere containing evidence of tumor on T2-weighted FLAIR images. Lesions exhibiting abnormal T2 hyperintensity on FLAIR images ("T2 lesions" volumes of interest) were manually contoured on all patients. To reduce the influence of outliers, the median and median absolute deviation of $MTR_{asym}$ and $R'_2$ within these regions were calculated, and the median absolute deviation was used to define variability for all measurements.

A Wilcoxon signed-rank test was used to determine whether averaging $MTR_{asym}$ from 2 gradient echoes resulted in a decrease in healthy-tissue $MTR_{asym}$ variability compared with a single gradient echo. For glioblastoma patients, volumes of interest of gadolinium contrast enhancement (CE) were segmented using T1 subtraction maps and a semi-automated thresholding method outlined previously. Regions of central necrosis were also delineated and examined. A paired t-test was used to determine whether $R'_2$ and $MTR_{asym}$ differed between T2-hyperintense lesions and NAWM. Within glioblastoma patients (WHO grade IV), a one-way repeated-measures analysis of variance (ANOVA) and Tukey's test for multiple comparisons was used to determine whether $R'_2$ or $MTR_{asym}$ at 3 ppm differed among regions of NAWM, T2 hyperintense lesions, regions of CE, and areas of central necrosis. An additional one-way ANOVA and Tukey's test for multiple comparisons was used to compare $R'_2$ or $MTR_{asym}$ at 3 ppm for T2 lesions across glioma grades II, III, and IV.

Figure 8:
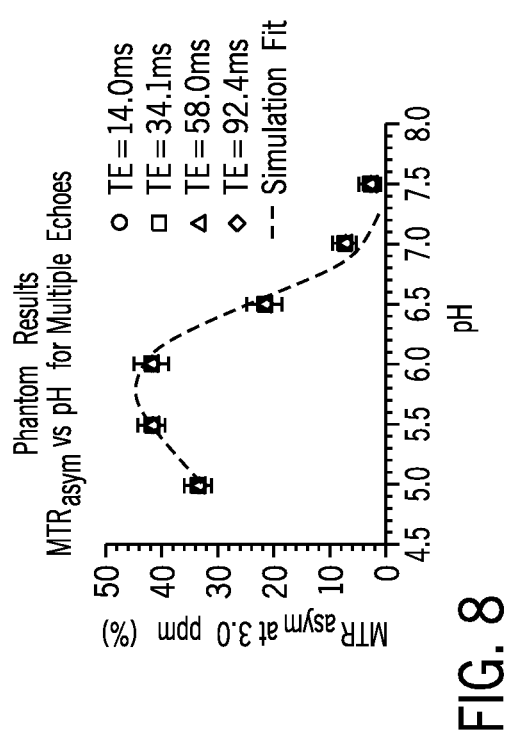
FIG. 8 is a graph of magnetization transfer ratio asymmetry ($MTR_{asym}$) data obtained by performing a CEST-SAGE-EPI pulse sequence on a glutamine phantom at various pH levels. The CEST contrast increases with decreasing pH within a physiological pH range similarly for all 4 echoes in an amino acid phantom and simulation estimates. These measurements closely match simulation estimates with measured or estimated relaxation and exchange rates.

The value of $MTR_{asym}$ at 3.0 ppm within each glutamine phantom, varying by pH, was similar across all 4 echoes, showing a characteristic increase in $MTR_{asym}$ at 3.0 ppm with decreasing pH (FIG. 8; ANOVA, p=0.999; comparison across echoes, p>0.99). These experimental results closely matched the simulation results using measured and theoretical relaxation and exchange rates (FIG. 8). The CNR was higher when averaging measurements from 2 gradient echoes (TE=14.1 ms and 34.1 ms) compared with a single gradient echo (TE=14.1 ms) in phantom samples containing the same concentration of glutamine, but varying pH.

In particular, CNR was approximately 13% higher when comparing pH=7.5 to 7.0 ($CNR_{1\&2}$=2.68; $CNR_1$=2.37), 7% higher when comparing pH=6.5 and 7.0 ($CNR_{1\&2}$=5.07; $CNR_1$=4.74), 15% higher when comparing pH=6.0 versus 7.0 ($CNR_{1\&2}$=17.2; $CNR_1$=15.0), and 6.5% higher when comparing pH=6.0 versus 6.5 ($CNR_{1\&2}$=6.72; $CNR_1$=6.31). Consistent with phantom results, the median $MTR_{asym}$ at 3.0 ppm in NAWM across all patients was not significantly different when using a single echo and the average of 2 gradient echoes (p=0.31); however, the median absolute deviation, a measure of variance in the measurements, was significantly lower when averaging the 2 gradient echoes (p=0.003).

Figure 9:
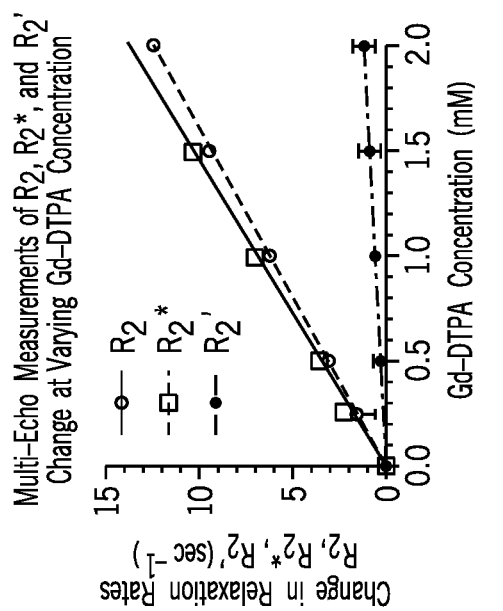
FIG. 9 is a graph that illustrates relaxometry measurements obtained using a CEST-SAGE-EPI pulse sequence in accordance with the present disclosure. The relaxometry measurements include $R_2$, $R^*_2$, and $R'_2$ at varying Gd-DTPA concentrations.
Figure 10:
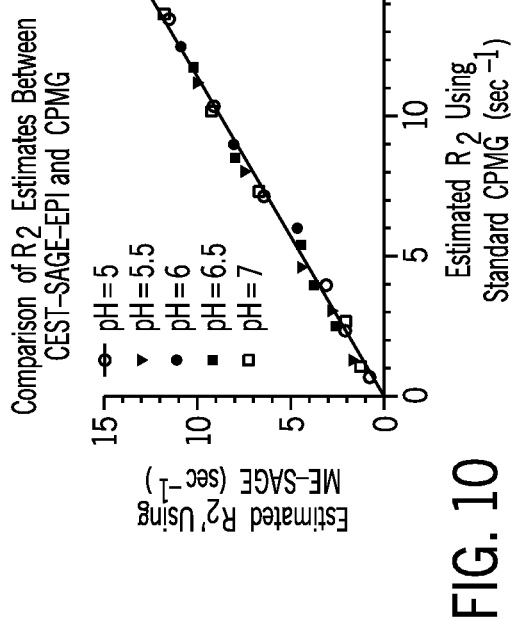
FIG. 10 is graph that illustrates a comparison between a measured $R^*_2$ using CEST-SAGE-EPI and Carr-Purcell-Meiboom-Gill (CPMG) performed during phantom. CEST-SAGE-EPI and CPMG show strong correlation ($R^2=0.9943$, $p<0.0001$), independent of pH ($p=0.9915$).

In phantom samples containing varying concentration of Gd-DTPA, CEST-SAGE-EPI estimates of $R_2$, $R^*_2$, and $R'_2$ varied linearly with concentration (FIG. 9), with estimates of transverse relaxivities of $R_2$=6.24±0.04 mM$^{-1}$ sec$^{-1}$. (p<0.0001), $R^*_2$=6.86+0.10 mM$^{-1}$ sec$^{-1}$ (p<0.0001), and R'2=0.61±0.08 mM$^{-1}$ sec$^{-1}$ (p=0.0007). Phantom results identified a strong, significant linear correlation between $R_2$ measurements using CEST-SAGE-EPI and CPMG (FIG. 10; $R_2$=0.9943, p<0.0001) and did not differ by pH (p=0.9915). Estimates of $R_2$ using CEST-SAGE-EPI, however, were lower than estimates of $R_2$ using standard CPMG measurements (slope=0.8845±0.006, p<0.0001 compared with slope=1), with CEST-SAGE-EPI estimates approximately 760 us lower on average than CPMG measurements (~7.1%).

Figure 11:
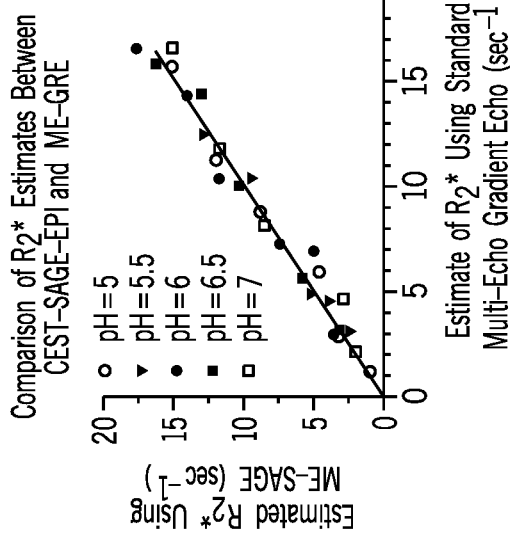
FIG. 11 is a graph that illustrates a comparison between measured $R'_2$ using CEST-SAGE-EPI and multi-echo gradient echo (ME-GRE) performed on a phantom. The comparison shows a strong correlation ($R^2=0.9727$, $p<0.0001$) and no dependence on pH ($p=0.2184$).
Figure 12:
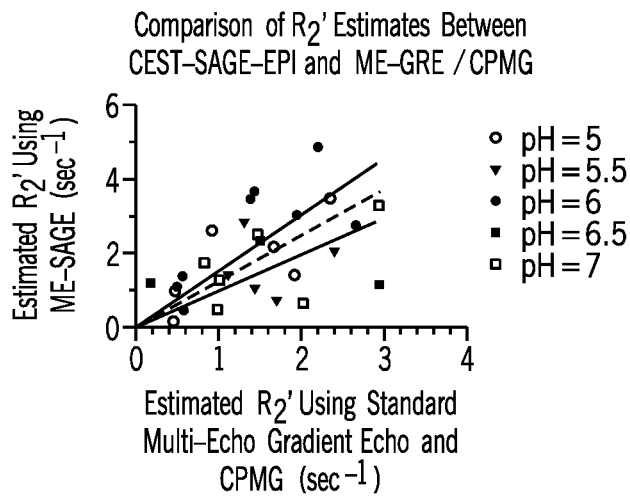
FIG. 12 is a graph that illustrates estimates of $R'_2$ obtained on a glutamine phantom using a subtraction of sequential CPMG and ME-GRE measurements and the CEST-SAGE-EPI method of the present disclosure. A comparison shows that the method the subtraction of sequential CPMG and ME-GRE measurements were not significantly different from those obtained using multi-echo SAGE EPI (slope=1.26±0.1301, p=0.0555) and did not differ by pH (p=0.0533).

A strong linear correlation was also observed between R*2 measurements obtained using CEST-SAGE-EPI and ME-GRE measurements (FIG. 11; $R_2$=0.9727, p<0.0001), and these measurements also did not differ by pH (p=0.2184). Estimates of $R^*_2$ were not significantly different from measurements obtained using standard ME-GRE measurements (slope=0.9862±0.0155, p=0.3819, showing no difference between slope=1). Consistent with these results, calculated estimates of $R'_2$ obtained through subtraction of sequential CPMG and ME-GRE measurements were congruent with SAGE-EPI measurements (FIG. 12; slope=1.26±0.1301, p=0.0555, showing no difference between slope=1) and did not differ by pH (p=0.0533).

Figure 13:
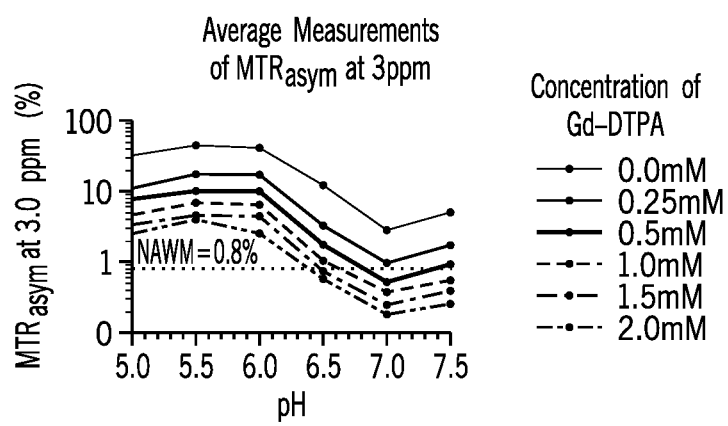
FIG. 13 is a graph illustrating average measurements of $MTR_{asym}$ at 3 ppm in accordance with the present disclosure.
Figure 14:
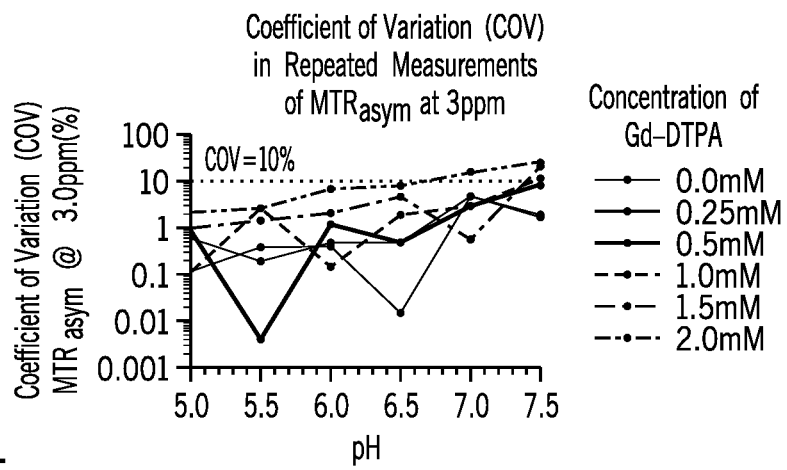
FIG. 14 is a graph illustrating the coefficient of variation measured from multiple test-retest experiments. The graph shows that the coefficient of variation is higher in the presence of contrast agents or in environments with shorter T1 and T2 characteristics.

Although measurements of transverse relaxation rate were not affected by pH, the relationship between $MTR_{asym}$ at 3.0 ppm and pH was affected by transverse relaxation rate (FIG. 13). Specifically, as transverse relaxation rates $R_2$ or $R^*_2$ increased as a result of increased concentration of Gd-DTPA, the sensitivity of $MTR_{asym}$ at 3.0 ppm to acidic pH decreased, particularly when concentrations were higher than 1 mM, corresponding to $T_2$ measurements of 150 to 170 ms and $T^*_2$=130 to 170 ms. Repeated experiments showed higher coefficient of variation with higher concentrations of Gd-DTPA, or lower $T_1$, as well as higher coefficient of variation with higher pH (FIG. 14).

Example 4: pH-Sensitive ($MTR_{asym}$) and Oxygen Sensitive ($R'_2$) Contrast Maps In vivo pH-sensitive and oxygen-sensitive MR images of human gliomas were taken using the methods presented herein. Qualitatively, the $T_2$ hyperintense lesions in all patients exhibited heterogeneous areas of both elevated $MTR_{asym}$ at 3.0 ppm (acidity) and $R'_2$ (hypoxia). Many areas of nonenhancing tumor in all patients exhibited uncharacteristically low measures of $R'_2$ despite evidence of elevated acidity, suggesting nonenhancing tumor regions may be adequately oxygenated and undergoing aerobic glycolysis. For example, a 42-year-old female with a nonenhancing recurrent World Health Organization (WHO) II isocitrate dehydrogenase (IDH) mutant astrocytoma (patient #43) exhibiting a region of focal acidity (high MTRasym at 3 ppm) and low oxygen consumption (low $R'_2$) was imaged. The image illustrated a WHO grade II astrocytoma with an area of moderately elevated acidity in the medial frontal lobe; however, this region exhibited $R'_2$ approximately 50% lower than surrounding NAWM.

In one non-limiting example, a 51-year-old male patient with a newly diagnosed nonenhancing IDH mutant WHO III anaplastic astrocytoma (patient #22) was also imaged. A lesion was identified and showed large, heterogeneous regions of abnormally high and low hypoxia and acidity. The image illustrated a large nonenhancing, isocitrate dehydrogenase (IDH) mutant WHO grade III astrocytoma with sizeable regions of macroscopic necrosis, as illustrated by T1 hypo-intensity. These areas of necrotic tissue exhibited both high levels of acidity and hypoxia, whereas the surrounding non-enhancing components with largely intact blood-brain barrier had elevated acidity, as suggested by higher MTRasym at 3.0 ppm, but lower levels of hypoxia, or $R'_2$, compared with regions of NAWM.

In another non-limiting example, a 53-year-old female patient with a recurrent IDH wild-type WHO IV glioblastoma was imaged that exhibited a region of focal acidity and large regions of low oxygen consumption (patient #15). Additionally, a 53-year-old female was imaged with a newly diagnosed IDH wild-type WHO IV glioblastoma (patient #3) displaying ring enhancement, central necrosis, elevated acidity, and oxygen extraction (hypoxia) within the enhancing region as well as low oxygen consumption in surrounding nonenhancing tumor. Each of the above female patient shad recurrent and newly diagnosed glioblastoma (WHO IV), respectively. Compared with the WHO grade II and III tumors with largely nonenhancing tumor with intact blood-brain barrier, patients with glioblastoma exhibited extensive areas of CE displayed both high acidity ($MTR_{asym}$ at 3.0 ppm) and hypoxia ($R'_2$) as well as regions of moderate acidity and oxygenated tumor.

Quantitative evaluation of various regions within these tumors confirmed these observations, as shown in FIGS. 15-23. Regions of $T_2$ hyperintense lesions exhibited a significantly lower median $R'_2$ (4.8±0.2 sec$^{-1}$) compared with NAWM (6.2±0.2 sec$^{-1}$) when pooling patients across all tumor grades (FIG. 15; paired t-test, p<0.0001). Within T2 hyper-intense lesions, the median $R'_2$ did not vary significantly across tumor grade (FIG. 16; ANOVA, p=0.0537; WHO II=4.6±0.4 sec$^{-1}$; WHO III=4.2±0.4 sec$^{-1}$; WHO II=5.4±0.3 sec$^{-1}$). In glioblastoma patients, significant differences in median $R'_2$ across tissue types were observed (FIG. 17; repeated-measures ANOVA, p=0.0001). In particular, the median $R'_2$ was significantly lower in T2 hyper-intense lesions (5.3±0.3 sec$^{-1}$) compared with both NAWM (6.3±0.2 sec$^{-1}$; Tukey's test, adjusted p=0.0078) and CE regions (10.0±1.0 sec$^{-1}$; Tukey's test, adjusted p=0.0002), whereas no difference was detected between T2 lesions and areas of central necrosis (4.0±0.5 sec$^{-1}$; Tukey's test, adjusted p=0.1499).

Additionally, the median $R'_2$ was significantly higher in CE lesions compared with NAWM (Tukey's test, adjusted p=0.0064) and necrosis (Tukey's test, adjusted p<0.0001), but significantly lower in necrosis compared with NAWM (Tukey's test, adjusted=0.0064). No differences in median $R'_2$ were observed between recurrent or newly diagnosed tumor or normal tissues (p>0.2), nor were significant differences observed between IDH mutant and wild-type tumors (p=0.12); however, IDH mutant tumors tended to have lower $R'_2$ compared with IDH wild-type tumors.

Median $MTR_{asym}$ at 3.0 ppm within T2 hyperintense lesions (1.7±0.1%) were significantly higher than NAWM (0.8±0.03%) when pooling all patients across grade (FIG. 18; paired t-test, p<0.0001). Within T2 hyperintense lesions, the median $MTR_{asym}$ at 3.0 ppm was significantly different across tumor grade (FIG. 19; ANOVA, p=0.0297), with WHO IV glioblastoma (2.0±0.2%) exhibiting significantly higher acidity compared with WHO II gliomas (1.5±0.1%; Tukey's test, adjusted p=0.0432). No difference was observed between WHO III gliomas (1.6±0.2%) compared with other grades (adjusted p>0.05). In a separate comparison, IDH mutant gliomas exhibited a slightly higher degree of tumor acidity compared with IDH wild-type tumors when correcting for grade (adjusted p=0.0434). Within WHO IV glioblastoma, significant differences in median $MTR_{asym}$ at 3.0 ppm were observed among various tissue types (FIG. 20; ANOVA, p<0.0001). Areas of macroscopic necrosis exhibited the highest $MTR_{asym}$ at 3.0 ppm degree of acidity ($MTR_{asym}$ at 3.0 ppm=4.4±0.4%) compared with all other tissue types, including CE lesions (2.9±0.1%; Tukey's test, adjusted p<0.0001), T2 hyperintense regions (2.0±0.2%, adjusted p<0.0001), and NAWM (0.8±0.04%, adjusted p<0.0001). Additionally, CE tumor exhibited significantly higher median $MTR_{asym}$ at 3.0 ppm compared with T2 hyper-intense lesions (Tukey's test, adjusted p=0.0218) and NAWM (Tukey's test, adjusted p<0.0001), whereas T2 lesions showed higher median $MTR_{asym}$ at 3.0 ppm (Tukey's test, adjusted p<0.0001).

Figure 21:
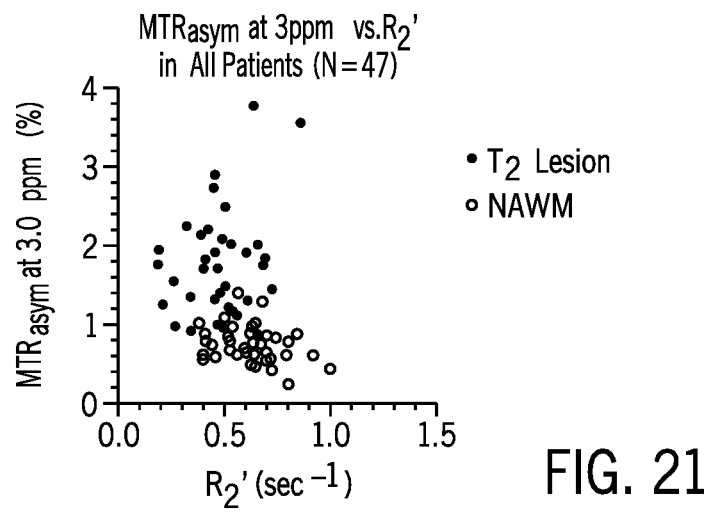
FIG. 21 is a graph that illustrates the value of $MTR_{asym}$ at 3 ppm (%) versus R'2 for NAWM and T2 hyperintense lesion in all patients pooled across tumor grades.
Figure 22:
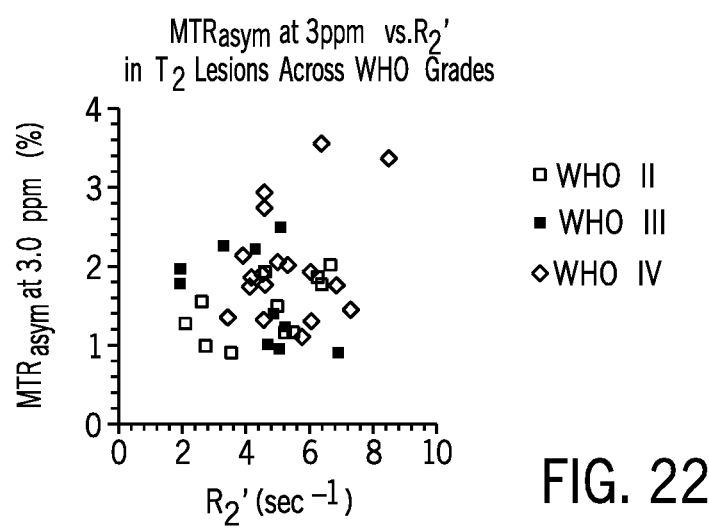
FIG. 22 is a graph that illustrates the value of $MTR_{asym}$ at 3 ppm (%) versus R'2 in T2 hyperintense regions for different tumor grades.

Examination of acidity and hypoxia characteristics within T2 hyperintense lesions pooled across tumor grade were markedly different from NAWM (FIG. 21), as T2 hyperintense lesions tended to be more acidic but slightly less hypoxic compared with NAWM. T2 hyperintense lesions did not show substantial separation across tumor grade (FIG. 22). Glioblastoma exhibited distinct characteristics across various tissue components (FIG. 23), with NAWM and T2 hyperintense lesions having relatively lower acidity and hypoxia combined with CE tumor and macroscopic necrotic tissue. The CE tumor exhibited a moderately high level of acidity, along with high degrees of oxygen extraction, whereas necrotic tissue showed low oxygen extraction yet high acidity.

Figure 23:
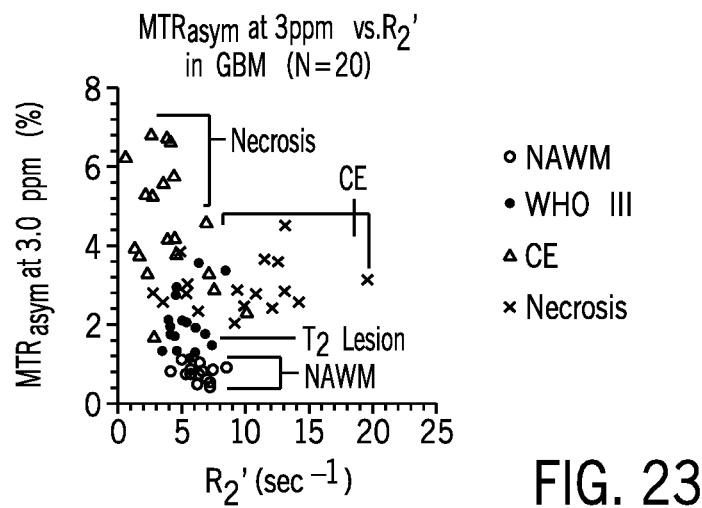
FIG. 23 is a graph that illustrates the value of $MTR_{asym}$ at 3 ppm (%) versus R'2 in different tissue types in GBM.

Mathematical simulations and phantom measurements confirmed the accuracy of the measurements provided herein. Consistent with tumor biology and the Warburg effect, we observed elevated acidity in tumor tissues even when there was adequate oxygen delivery due to an intact BBB, high neovascularity, and high blood flow. In particular, we observed lower levels of hypoxia and high acidity in regions of nonenhancing tumor (T2/FLAIR hyperintensity) (FIGS. 15 and 18; FIGS. 21 and 23), which can have elevated vascularity depending on the degree of malignancy and/or grade. This was similar across tumor grade, although glioblastoma had slightly higher levels of hypoxia compared with lower grades. In the same tumors we observed substantially higher levels of hypoxia in areas of CE (FIG. 11; FIG. 17; FIGS. 21 and 23), which is known to be the most aggressive and hypoxic. These data suggest that tumor acidity and oxygen consumption are both complex and spatially heterogeneous, consistent with the known genetic, histopathologic, proteomic, and metabolic spatial heterogeneity. Hypoxic, nonhypoxic, and/or acidic tumors may also have differing therapeutic responses, as tumor hypoxia and acidity are both known to reduce sensitivity to chemoradiation.

High-resolution pH-sensitive and oxygen-sensitive MR imaging contrast in brain tumors can be achieved on clinical 3T MR systems by implementing a multi-echo SAGE-EPI readout after off-resonance saturation or CEST preparation of amine protons (3.0 ppm). Comparable techniques for CEST imaging that take advantage of multiple echo readouts are relatively limited. Compared to conventional techniques, CEST-SAGE-EPI has many advantages including speed, in-line B0 mapping, whole-brain coverage, and simultaneous CEST, $R_2$, $R^*_2$, and $R'_2$ quantitation.

The present disclosure has described one or more preferred embodiments, and it should be appreciated that many equivalents, alternatives, variations, and modifications, aside from those expressly stated, are possible and within the scope of the invention.

The invention claimed is:

1. A method for producing a pH-sensitive and an oxygen-sensitive magnetic resonance (MR) image in a region of interest of a subject, the method comprising:
    applying at least one radiofrequency (RF) saturation pulse at a frequency or a range of frequencies to substantially saturate magnetization corresponding to an exchangeable proton in the region of interest to generate magnetic resonance data;
    performing an echo-planar imaging (EPI) readout to acquire the magnetic resonance data generated in response to applying the at least one RF saturation pulse by sampling in each of a plurality of repetition time periods a first gradient echo pulse train at a first echo time, a second gradient echo pulse train in a second echo time, a first spin echo train at a third echo time, and a second spin echo at a fourth echo train;
    computing one or more relaxometry measurement using the magnetic resonance data sampled at the first echo time, the second echo time, the third echo time, and the fourth echo time;
    generating a pH-weighted image based on the magnetic resonance data sampled at one or more of the first echo time, the second echo time, the third echo time, and the fourth echo time; and
    generating an oxygen-weighted image based on the one or more relaxometry measurement.

2. The method of claim 1, wherein the pH-weighted image and the oxygen-weighted image are generated simultaneously.

3. The method of claim 1, wherein the pH-weighted image is indicative of a concentration of the exchangeable proton within the region of interest.

4. The method of claim 1, wherein the oxygen-weighted image is indicative of a concentration of deoxyhemoglobin within the region of interest.

5. The method of claim 1, wherein the magnetic resonance data comprises chemical exchange saturation transfer (CEST) data, and wherein the method further comprises processing the CEST data to generate a magnetization transfer ratio ($MTR_{asym}$) corresponding to the exchangeable proton within the region of interest, and wherein the pH-weighted image includes a contrast map of the magnetization transfer ratio.

6. The method of claim 5, wherein the pH-weighted image is generated using the magnetic resonance data acquired at the first echo time and the second echo time.

7. The method of claim 1, further comprising applying the at least one RF saturation pulse at the range of frequencies corresponding to an amine exchangeable proton in the region of interest.

8. The method of claim 1, wherein the one or more relaxometry measurement includes a reversible transverse relaxation rate ($R'_2$), and wherein the oxygen-weighted image includes a contrast map of the reversible transverse relaxation rate.

9. The method of claim 1, wherein first spin echo pulse train includes an asymmetric spin echo pulse train.

10. The method of claim 1, wherein the pH-weighted image is generated using an average of the magnetic resonance data acquired at the first echo time and the second echo time.

11. The method of claim 1, wherein at least one radiofrequency (RF) saturation pulse includes off-resonance chemical exchange saturation transfer (CEST) RF pulses, wherein the off-resonance CEST RF pulses includes a train of three Guassian pulses.

12. The method of claim 1, wherein the at least one radiofrequency (RF) saturation pulse includes a spectral-spatial water excitation pulse configured before the echo-planar imaging readout.

13. The method of claim 1 further comprising applying a refocusing pulse that is configured between the second gradient echo pulse train and the first spin echo pulse train.

14. The method of claim 13, wherein the refocusing pulse comprises a 180 degree refocusing pulse.

15. The method of claim 1, wherein the region of interest includes a suspected ischemic region on the subject, and wherein the method further comprises displaying the pH-weighted image and the oxygen-weighted image on a display, and wherein the pH-weighted image is generated to exhibit a positive contrast for ischemic regions, and wherein the oxygen-weighted image is configured to display a negative contrast for ischemic regions.

16. The method of claim 1, wherein the region of interest includes a suspected traumatic injury that includes micro- or macroscopic bleeding, and wherein the method further comprises displaying the pH-weighted image and the oxygen-weighted image on a display, and wherein the pH-weighted image is generated to exhibit a negative contrast for regions that include micro- or macroscopic bleeding, and wherein the oxygen-weighted image is configured to display a positive contrast for regions that include micro- or macroscopic bleeding.

17. A method for producing a pH-sensitive and an oxygen-sensitive magnetic resonance (MR) image in a region of interest of a subject, the method comprising:

applying at least one radiofrequency (RF) saturation pulse at a frequency or a range of frequencies to substantially saturate magnetization corresponding to an exchangeable proton in the region of interest to generate magnetic resonance data;

performing an echo-planar imaging (EPI) readout to acquire magnetic resonance data in response to applying the at least one RF saturation pulse by sampling a series of gradient echo pulse trains at a series of gradient echo times and sampling a series of spin echo pulse trains at a series of spin echo times;

computing one or more relaxometry measurement using the magnetic resonance data sampled at the gradient echo times and the spin echo times;

generating a pH-weighted image based on the magnetic resonance data sampled at one or more of the gradient echo times and spin echo times;

generating an oxygen-weighted image based on the one or more relaxometry measurement.

18. The method of claim 17, wherein the pH-weighted image and the oxygen-weighted image are generated simultaneously.

19. The method of claim 17, wherein the magnetic resonance data comprises chemical exchange saturation transfer (CEST) data, and wherein the method further comprises processing the CEST data to generate a magnetization transfer ratio ($MTR_{asym}$) corresponding to the exchangeable proton within the region of interest, and wherein the pH-weighted image includes a contrast map of the magnetization transfer ratio.

20. The method of claim 17, wherein the one or more relaxometry measurement includes a reversible transverse relaxation rate ($R'_2$), and wherein the oxygen-weighted image includes a contrast map of the reversible transverse relaxation rate.

21. A system comprising:

a magnet system configured to generate a polarizing magnetic field about at least a portion of a subject;

a magnetic gradient system including a plurality of magnetic gradient coils configured to apply at least one magnetic gradient field to the polarizing magnetic field;

a radio frequency (RF) system configured to apply an RF field to the subject and to receive magnetic resonance signals from the subject using a coil array;

a computer system programmed to:

apply at least one radiofrequency (RF) saturation pulse at a frequency or a range of frequencies to substantially saturate magnetization corresponding to an exchangeable proton in the region of interest to generate magnetic resonance data;

perform an echo-planar imaging (EPI) readout to acquire the magnetic resonance data generated in response to applying the at least one RF saturation pulse by sampling in each of a plurality of repetition time periods a first gradient echo pulse train at a first echo time, a second gradient echo pulse train in a second echo time, a first spin echo train at a third echo time, and a second spin echo at a fourth echo train;

compute one or more relaxometry measurement using the magnetic resonance data sampled at the first echo time, the second echo time, the third echo time, and the fourth echo time;

generate a pH-weighted image based on the magnetic resonance data sampled at one or more of the first echo time, the second echo time, the third echo time, and the fourth echo time; and generate an oxygen-weighted image based on the one or more relaxometry measurement.

* * * * *